United States Patent [19]
Daluge

[11] Patent Number: 5,399,580
[45] Date of Patent: Mar. 21, 1995

[54] THERAPEUTIC NUCLEOSIDES-USES

[75] Inventor: Susan M. Daluge, Chapel Hill, N.C.

[73] Assignee: Burroughs Wellcome Co., Research Triangle Park, N.C.

[21] Appl. No.: 127,461

[22] Filed: Sep. 27, 1993

Related U.S. Application Data

[63] Continuation of Ser. No. 28,020, Mar. 8, 1993, abandoned.

[51] Int. Cl.$^6$ .............................................. A61K 31/415
[52] U.S. Cl. .................................... 514/394; 514/387; 514/395
[58] Field of Search ......................... 514/387, 394, 395

[56] References Cited

U.S. PATENT DOCUMENTS

| | | | |
|---|---|---|---|
| 4,492,708 | 1/1985 | Spitzer | 424/273 B |
| 5,039,689 | 8/1991 | Daluge | 514/359 |

FOREIGN PATENT DOCUMENTS

| | | |
|---|---|---|
| 0334361 | 9/1989 | European Pat. Off. . |
| 0347852 | 12/1989 | European Pat. Off. . |
| 0368640A3 | 5/1990 | European Pat. Off. . |
| 0431799A2 | 6/1991 | European Pat. Off. . |

OTHER PUBLICATIONS

Raegmaeheis et al 90CA:54975y 1979.

*Primary Examiner*—Raymond J. Henley, III
*Assistant Examiner*—Russell Travers
*Attorney, Agent, or Firm*—Lawrence A. Nielsen

[57] ABSTRACT

Antiviral nucleoside analogues containing a substituted benzimidazole base attached to a carbocyclic ring in place of the conventional sugar residue, particularly those in which the 2-, 5- and 6-positions of the benzimidazole base are substituted by halogen, have activity against hepatitis B virus infections.

20 Claims, No Drawings

THERAPEUTIC NUCLEOSIDES-USES

This is a continuation of copending application Ser. No. 08/028,020, filed on Mar. 8, 1993, now abandoned.

The present invention relates to purine nucleoside analogues containing a carbocyclic ring in place of the sugar residue, pharmaceutically acceptable derivatives thereof, and their use in medical therapy, particularly for the treatment of certain viral infections.

Hepatitis B virus (HBV) is a small DNA containing virus which infects humans. It is a member of the class of closely related viruses known as the hepadnaviruses, each member of which selectively infects either mammalian or avian hosts, such as the woodchuck and the duck.

Worldwide, HBV is a viral pathogen of major consequence. It is most common in Asian countries, and prevalent in sub-Saharan Africa. The virus is etiologically associated with primary hepatocellular carcinoma and is thought to cause 80% of the world's liver cancer. In the United States more than ten thousand people are hospitalized for HBV illness each year, an average of 250 die with fulminant disease.

The United States currently contains an estimated pool of 500,000-1 million infectious carriers. Chronic active hepatitis will develop in over 25% of carriers, and often progresses to cirrhosis. It is estimated that 5000 people die from HBV-related cirrhosis each year in the USA, and that perhaps 1000 die from HBV-related liver cancer. Even when a universal HBV vaccine is in place, the need for effective anti-HBV compounds will continue. The large reservoir of persistently infected carriers, estimated at 220 million worldwide, will receive no benefit from vaccination and will continue at high risk for HBV-induced liver disease. This carrier population serves as the source of infection of susceptible individuals perpetuating the instance of disease particularly in endemic areas or high risk groups such as IV drug abusers and homosexuals. Thus, there is a great need for effective antiviral agents, both to control the chronic infection and reduce progression to hepatocellular carcinoma.

Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease as outlined above.

In "Viral Infections of Humans" (second edition, Ed., Evans, A. S. (1982) Plenum Publishing Corporation, New York), Chapter 12 describes in detail the etiology of viral hepatitis infections.

Of the DNA viruses, the herpes group is the source of many common viral illnesses in man. The group includes cytomegalovirus (CMV), Epstein-Barr virus (EBV), varicella zoster virus (VZV), herpes simplex virus (HSV) and human herpes virus 6 (HHV6).

In common with other herpes viruses, infection with CMV leads to a life-long association of virus and host and, following a primary infection, virus may be shed for a number of years. Clinical effects range from death and gross disease (microcephaly, hepatosplenemegaly, jaundice, mental retardation) through failure to thrive, susceptibility to chest and ear infections to a lack of any obvious ill effect. CMV infection in AIDS patients is a predominant cause of morbidity as, in 40 to 80% of the adult population, it is present in a latent form and can be reactivated in immunocompromised patients.

EBV causes infectious mononucleosis and is also suggested as the causative agent of nasopharyngeal cancer, immunoblastic lymphoma, Burkitt's lymphoma and hairy leukoplakia.

VZV causes chicken pox and shingles. Chicken pox is the primary disease produced in a host without immunity. In young children, it is usually a mild illness characterized by a vesicular rash and fever. Shingles is the recurrent form of the disease which occurs in adults who were previously infected with varicella. The clinical manifestations of shingles include neuralgia and a vesicular skin rash that is unilateral and dermatomal in distribution. Spread of inflammation may lead to paralysis or convulsions and coma can occur if the meninges becomes affected. In immunodeficient patients, VZV may disseminate causing serious or even fatal illness.

HSV 1 and HSV 2 are some of the most common infectious agents of man. Most of these viruses are able to persist in the host's neural cells. Once infected, individuals are at risk of recurrent clinical manifestation of infection which can be both physically and psychologically distressing. HSV infection is often characterized by extensive lesions of the skin, mouth and/or genitals. Primary infections may be subclinical although they tend to be more severe than infections in individuals previously exposed to the virus. Ocular infections by HSV can lead to keratitis or cataracts. Infection in the newborn, in immunocompromised patients or penetration of infection into the central nervous system can prove fatal. HHV6 is the causative agent of roseola infantum (exanthum subitum) in children which is characterized by fever and the appearance of a rash after the fever has declined. HHV6 has also been implicated in syndromes of fever and/or rash and pneumonia or hapatitis in immunocompromised patients.

It has now been discovered that certain substituted benzimidazole compounds as referred to below, are useful for the treatment or prophylaxis of certain viral infections. According to a first aspect of the present invention, novel compounds of the formulas (I) and (I-1) are provided:

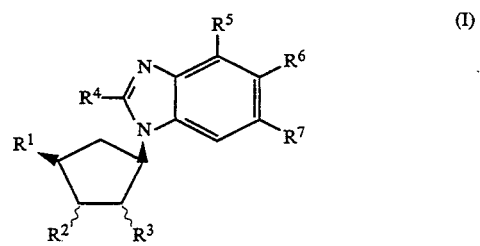

(I)

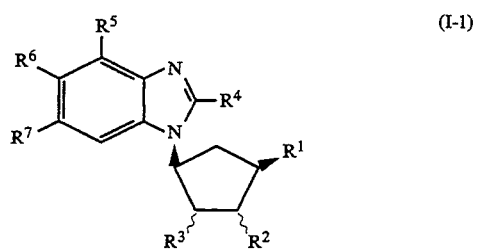

(I-1)

wherein
$R^1$ is H, $CH_3$ or $CH_2OH$;
$R^2$ is H or OH;

$R^3$ is H or OH;
or $R^2$ and $R^3$ together form a bond;
$R^4$ is H, Cl, Br, I, $C_{1-4}$ alkyl, $C_{3-7}$cycloalkyl, $C_{3-7}$cycloalkyl$C_{1-4}$alkyl, $C_{1-4}$ perfluoroalkyl (e.g., trifluoromethyl), $NH_2$, $C_{1-4}$ alkylamino, $C_{1-4}$ dialkylamino, $C_{3-7}$cycloalkylamino, di$C_{3-7}$cycloalkylamino, N-$C_{1-4}$alkyl-N-$C_{3-7}$cycloalkylamino, N-$C_{1-4}$alkyl-N-$C_{3-7}$cycloalkyl$C_{1-4}$alkylamino, di$C_{3-7}$cycloalkyl$C_{1-4}$alkylamino, $C_{3-7}$cycloalkyl$C_{1-4}$alkylamino, N-$C_{3-7}$cycloalkyl-N-$C_{3-7}$cycloalkyl$C_{1-4}$alkylamino, SH, $C_{1-4}$ alkylthio, $C_{6-10}$aryl$C_{1-4}$alkylthio, OH, $C_{1-4}$ alkoxy, $C_{6-10}$aryl$C_{1-4}$alkyoxy or $C_{6-10}$aryl$C_{1-4}$alkyl; and $R^5$, $R^6$ and $R^7$ are independently selected from H, F, Cl, Br, I, $CF_3$ and $CH_3$, provided that at least one of $R^1$, $R^2$ and $R^3$ is or contains OH; and pharmaceutically acceptable derivatives thereof.

Preferred compounds of formula (I) and (I-1) are those show in formula (IA) and (IA-1):

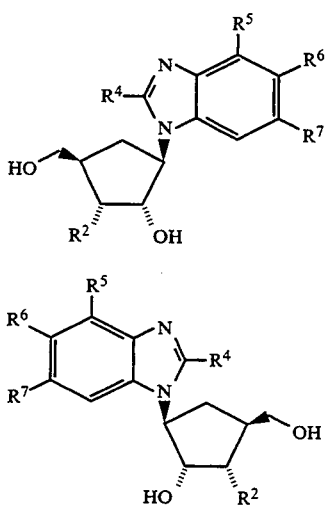

(IA)

(IA-1)

wherein $R^2$ is H or OH.

Most preferred compounds of formulas (I), (I-1), (IA), and (IA-1) are those wherein $R^4$ is $CH_3$, Cl or Br; $R^5$ is H; and $R^6$ and $R^7$ are each Cl.

It is to be understood that the present invention encompasses the particular enantiomers depicted in formula (I) and (I-1), including tautomers of the purine, alone and in combination with their mirror-image enantiomers. Enantiomers depicted by formula (I) are preferred and preferably are provided substantially free of the corresponding enantiomer to the extent that it is generally in admixture with less than 10% w/w, preferably less than 5% w/w, more preferably less than 2% w/w and most preferably less than 1% w/w of the corresponding enantiomer based on the total weight of the mixture. Enantiomers depicted by formula (I-1) are most preferred and preferably are provided substantially free of the corresponding enantiomer to the extent that it is generally in admixture with less than 10% w/w, preferably less than 5% w/w, more preferably less than 2% w/w and most preferably less than 1% w/w of the corresponding enantiomer based on the total weight of the mixture.

Particularly preferred examples of compounds of formula (I) are:

(1R,2S,3S,5S)-5-(2-Bromo-5,6-dichloro-1H-benzimidazol-1-yl)-3-(hydroxymethyl)-1,2-cyclopentanediol
(1S,2R,3R,5R)-5-(2-Bromo-5,6-dichloro-1H-benzimidazol-1-yl)-3-(hydroxymethyl)-1,2-cyclopentanediol
(±)-(1R*,2R*,4S*)-2-(2-Bromo-5,6-dichloro-1H-benzimidazol-1-yl)-4-(hydroxymethyl)-cyclopentanol;
(±)-(1R*,2S*,3S*,5S*)-5-(2-bromo-5,6-dichloro-1H-benzimidazol-1-yl)-3-(hydroxymethyl)-1,2-cyclopentanediol;
(±)-(1R*,2S*,3S*,5S*)-5-(2,5,6-trichloro-1H-benzimidazol-1-yl)-3-(hydroxymethyl)-1,2-cyclopentanediol;
(±)-(1R*,2S*,3R*)-3-(2-bromo-5,6-dichloro-1H-benzimidazol-1-yl)-1,2-cyclopentanediol; and
(±)-(1R*,2S*,3S*,5S*)-5-(5,6-Dichloro-2-methyl-1H-benzimidazol-1-yl)-3-(hydroxymethyl)-1,2-cyclopentanediol
and pharmaceutically acceptable salts thereof.

The compounds of formulas (I) and (I-1) above and their pharmaceutically acceptable derivatives are herein referred to as the compounds according to the invention.

In a further aspect of the invention there are provided the compounds according to the invention for use in medical therapy particularly for the treatment or prophylaxis of viral infections such as herpes viral infections. To date compounds of the invention have been shown to be active against hepatitis B virus (HBV) and cytomegalovirus (CMV) infections, although early results suggest that the invention could also be active against other herpes virus infections such as EBV, VZV, HSVI and II and HHV6.

Other viral conditions which may be treated in accordance with the invention have been discussed in the introduction hereinbefore.

In yet a further aspect of the present invention there is provided:

a) A method for the treatment or prophylaxis of a hepadnaviral infection such as hepatitis B or a herpes viral infection such as CMV which comprises treating the subject with a therapeutically effective amount of a compound according to the invention.

b) Use of a compound according to the invention in the manufacture of a medicament for the treatment or prophylaxis of any of the above-mentioned infections or conditions.

By "a pharmaceutically acceptable derivative" is meant any pharmaceutically or pharmacologically acceptable salt, ester or salt of such ester of a compound according to the invention, or any compound which, upon administration to the recipient, is capable of providing (directly or indirectly) a compound according to the invention, or an antivirally active metabolite or residue thereof.

Preferred esters of the compounds of the invention include carboxylic acid esters in which the non-carbonyl moiety of the ester grouping is selected from straight or branched chain alkyl, e.g. n-propyl, t-butyl, n-butyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy or amino); sulfonate esters such as alkyl- or aralkylsulfonyl (e.g. methanesulfonyl); amino acid esters (e.g. L-valyl or L-isoleucyl); and mono-, di- or triphosphate esters. The phosphate esters may be further esterified by, for example, a $C_{1-20}$ alcohol or reactive derivative thereof, or by a 2,3-di(C$_{6-24}$)acyl glycerol.

With regard to the above-described esters, unless otherwise specified, any alkyl moiety present advantageously contains 1 to 18 carbon atoms, particularly 3 to 6 carbon atoms such as the pentanoate. Any aryl moiety present in such esters advantageously comprises a phenyl group.

Any reference to any of the above compounds also includes a reference to a pharmaceutically acceptable salt thereof.

Physiologically acceptable salts include salts of organic carboxylic acids such as acetic, lactic, tartaric, malic, isethionic, lactobionic, p-aminobenzoic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

The above compounds according to the invention and their pharmaceutically acceptable derivatives may be employed in combination with other therapeutic agents for the treatment of the above infections or conditions. Examples of such further therapeutic agents include agents that are effective for the treatment of viral infections or associated conditions such as acyclic nucleosides (e.g. acyclovir), immunomodulatory agents such as thymosin, ribonucleotide reductase inhibitors such as 2-acetylpyridine 5-[(2-chloroanilino)thiocarbonyl)thiocarbonohydrazone, interferons such as $\alpha$-interferon, 1-$\beta$-D-arabinofuranosyl-5-(1-propynyl)uracil, 3'-azido-3'-deoxythymidine, ribavirin and phosphonoformic acid. The component compounds of such combination therapy may be administered simultaneously, in either separate or combined formulations, or at different times, e.g. sequentially such that a combined effect is achieved.

The compounds according to the invention, also referred to herein as the active ingredient, may be administered for therapy by any suitable route including oral, rectal, nasal, topical (including transdermal, buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 1.0 to 20 mg per kilogram body weight per day. (Unless otherwise indicated, all weights of active ingredient are calculated as the parent compound of formula (I); for salts or esters thereof, the weights would be increased proportionally.) The desired dose is preferably presented as two, three, four, five, six or more sub-doses administered at appropriate intervals throughout the day. These sub-doses may be administered in unit dosage forms, for example, containing 10 to 1000 mg, preferably 20 to 500 mg, and most preferably 100 to 400 mg of active ingredient per unit dosage form.

Ideally, the active ingredient should be administered to achieve peak plasma concentrations of the active compound of from about 0.025 to about 100 $\mu$M, preferably about 0.1 to 70 $\mu$M, most preferably about 0.25 to 50 $\mu$M. This may be achieved, for example, by the intravenous injection of a 0.1 to 5% solution of the active ingredient, optionally in saline, or orally administered as a bolus containing about 0.1 to about 250 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation. The formulations of the present invention comprise at least one active ingredient, as defined above, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including transdermal buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research*, 3 (6), 318 (1986).

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The present invention further includes the following process, depicted schematically, for the preparation of compounds of formula (I) above and derivatives thereof either alone or in combination with their corresponding enantiomers.

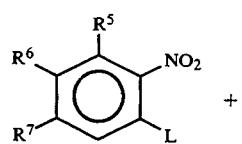

(Wherein L is a leaving group, e.g., halogen, in particular Chloro)

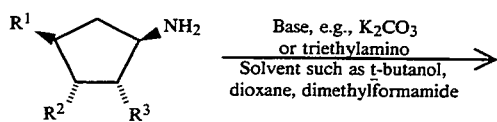

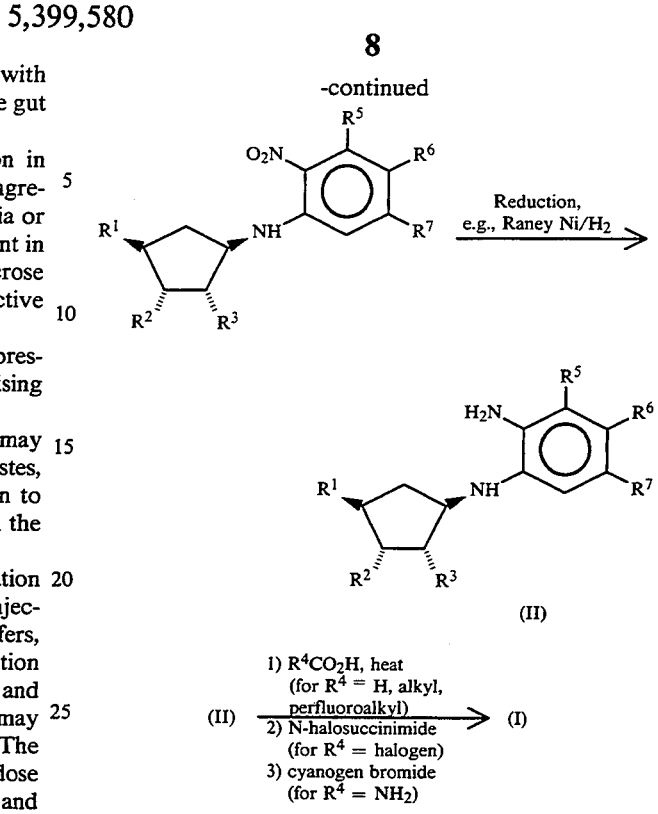

Compounds of formulas (I), and (I-1) wherein $R^4$ is halogen, e.g., chloro, may be converted into compounds of formulas (I) and (I-1) wherein $R^4$ is SH (or S alkyl) OH (or alkoxide) by methods well known in the art, for example, by reaction with an alcoholic solution of NaHs (or NaS alkyl) or aqueous NaOH (or alcoholic Na alkoxide), respectively.

Thus, according to a further feature of the present invention we provide a process for the preparation of compounds of formulae (I) and (I-1) alone or in combination with their mirror image enantiomers, and their pharmaceutically acceptable derivatives which comprises (A) reacting

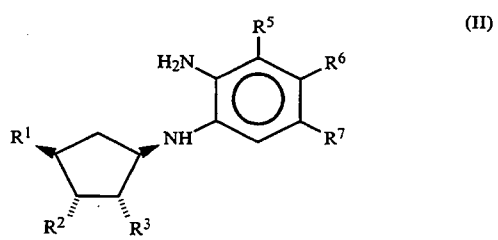

or the mirror image enantiomer thereof, with
  a) either a compound of formula $R^4CO_2H$ wherein $R^4$ is H, $C_{1-4}$ alkyl or $C_{1-4}$ perfluoroalkyl preferably at an elevated temperature or a compound of formula $R^4C(OR)_3$ wherein $R^4$ is H, $C_{1-4}$ alkyl or $C_{1-4}$ perfluoroalkyl and R is $C_{1-4}$ alkyl, preferably at ambient temperature and in an acidic medium, to form a compound of formula (I) or (I-1) in which $R^4$ is H, $C_{1-4}$ alkyl or $C_{1-4}$ perfluoroalkyl; or
  b) cyanogen bromide to form a compound of formula (I) or (I-1) in which $R^4$ is $NH_2$; or
  c) 1,1'-carbonyl-diimidazole to form a compound of formula (I) or (I-1) in which $R^4$ is OH; or d) 1,1′-thiocarbonyl-diimidazole or thiourea to form a compound of formula (I) or (I-1) in which $R^4$ is SH; or (B)
a) converting a compound of formula (I) or (I-1) in which $R^4$ is hydrogen into a further compound of formula (I) or (I-1) in which $R^4$ is a different group for example by treatment with an N-(Cl, Br or I) succinimide to form a compound in which $R^4$ is Cl, Br or I; or b) converting a compound of formula (I) or (I-1) in which $R^4$ is Cl, Br or I into a further compound of formula (I) or (I-1) in which $R^4$ is a different group as defined above, for example by treatment with an alcoholic NaHS or NaS-$C_{1-4}$alkyl, e.g. in alcoholic solution to form compounds in which $R^4$ is SH or $C_{1-4}$ alkylthio respectively, by treatment with for example, aqueous NaOH or alcoholic Na-$C_{1-4}$ alkoxide to form compounds in which $R^4$ is OH or $C_{1-4}$ alkoxy or by treatment with a $C_{1-4}$ alkylamine or di-$C_{1-4}$ alkylamine to form compounds in which $R^4$ is $C_{1-4}$ alkylamino or di-$C_{1-4}$ alkylamino; or (C) reacting a compound of formula

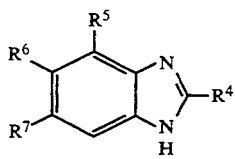

(III)

(wherein $R^4$ is hydrogen and $R^5$, $R^6$ and $R^7$ are as hereinbefore defined) or a functional equivalent thereof with a compound of formula

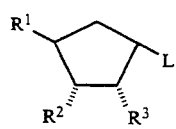

(IV)

wherein $R^1$, $R^2$ and $R^3$ are as defined above and L is a leaving group, for example an organosulphonyloxy (e.g. p-toluenesulphonyloxy or methanesulphonyloxy), halogen or triflate ($OSO_2CF_3$) group, for example in the presence of a base such as sodium carbonate or sodium hydride in a solvent such as dimethylformamide, advantageously at an elevated temperature e.g. 80°–100° C., to form a compound of formula (I) or (I-1) in which $R^4$ is hydrogen; and optionally converting a compound of formula (I) or (I-1) into a pharmaceutically acceptable derivative thereof.

Alternatively in process (C) above the compound of formula (IV) may be replaced with a compound in which the L and $R^3$ groups are replaced with a cyclic sulphate group.

All of the structures shown above are intended to represent the enantiomers depicted as well as their mirror image isomers, as well as mixtures thereof. Thus, the present invention is intended to encompass both the racemates and the pure enantiomers, substantially free of their mirror-image isomers.

A compound of formula (I) or (I-1) may be converted into a pharmaceutically acceptable ester by reaction with an appropriate esterifying agent, e.g. an acid halide or anhydride. The compound of formula (I) or (I-1) including esters thereof, may be converted into pharmaceutically acceptable salts thereof in conventional manner, e.g. by treatment with an appropriate acid. An ester or salt of an ester of formula (I) or (I-1) may be converted into the parent compound, e.g. by hydrolysis.

The following Examples are intended for illustration only and are not intended to limit the scope of the invention in any way. The term 'active ingredient' as used in the examples means a compound of formula (I) or (I-1) or a pharmaceutically acceptable derivative thereof.

EXAMPLE A

Tablet Formulations

The following formulations A and B were prepared by wet granulation of the ingredients with a solution of povidone, followed by addition of magnesium stearate and compression.

| Formulation A | mg/tablet | mg/tablet |
|---|---|---|
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
| | 500 | 300 |
| Formulation B | | |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
| | 500 | 300 |
| Formulation C | mg/tablet | |
| Active ingredient | 100 | |
| Lactose | 200 | |
| Starch | 50 | |
| Povidone | 5 | |
| Magnesium stearate | 4 | |
| | 359 | |

The following formulations, D and E, were prepared by direct compression of the admixed ingredients. The lactose used in formulation E was of the direct compression type (Dairy Crest—"Zeparox").

| | mg/tablet |
|---|---|
| Formulation D | |
| Active Ingredient | 250 |
| Pregelatinised Starch NF15 | 150 |
| | 400 |
| Formulation E | |
| Active Ingredient | 250 |
| Lactose | 150 |
| Avicel | 100 |
| | 500 |

Formulation F (Controlled Release Formulation)

The formulation was prepared by wet granulation of the ingredients (below) with a solution of povidone followed by the addition of magnesium stearate and compression.

| | mg/tablet |
|---|---|
| (a) Active Ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |

-continued

| | mg/tablet |
|---|---|
| | 700 |

EXAMPLE B

Capsule Formulations

Formulation A

A capsule formulation was prepared by admixing the ingredients of Formulation D in Example 1 above and filling into a two-part hard gelatin capsule. Formulation B (infra) was prepared in a similar manner.

| Formulation B | mg/capsule |
|---|---|
| (a) Active ingredient | 250 |
| (b) Lactose B.P. | 143 |
| (c) Sodium Starch Glycollate | 25 |
| (d) Magnesium Stearate | 2 |
| | 420 |
| Formulation C | |
| (a) Active ingredient | 250 |
| (b) Macrogol 4000 BP | 350 |
| | 600 |

Capsules were prepared by melting the macrogol 4000 BP, dispersing the active ingredient in the melt and filling the melt into a two-part hard gelatin capsule.

| Formulation D | mg/capsule |
|---|---|
| Active ingredient | 250 |
| Lecithin | 100 |
| Arachis Oil | 100 |
| | 450 |

Capsules were prepared by dispersing the active ingredient in the lecithin and arachis oil and filling the dispersion into soft, elastic gelatin capsules.

Formulation E (Controlled Release Capsule)

The following controlled release capsule formulation was prepared by extruding ingredients a, b and c using an extruder, followed by spheronisation of the extrudate and drying. The dried pellets were then coated with release-controlling membrane (d) and filled into a two-piece, hard gelatin capsule.

| | mg/capsule |
|---|---|
| (a) Active Ingredient | 250 |
| (b) Microcrystalline Cellulose | 125 |
| (c) Lactose BP | 125 |
| (d) Ethyl Cellulose | 13 |
| | 513 |

EXAMPLE C

Injectable Formulation

| Formulation A. | |
|---|---|
| Active ingredient | 0.200 g |
| Hydrochloric acid solution, 0.1M | q.s. to pH 4.0 to 7.0 |
| Sodium hydroxide solution, 0.1M | q.s. to pH 4.0 to 7.0 |
| Sterile water | q.s. to 10 ml |

The active ingredient was dissolved in most of the water (35°–40° C.) and the pH adjusted to between 4.0 and 7.0 with the hydrochloric acid or the sodium hydroxide as appropriate. The batch was then made up to volume with the water and filtered through a sterile micropore filter into a sterile 10ml amber glass vial (type 1) and sealed with sterile closures and overseals.

| Formulation B. | |
|---|---|
| Active ingredient | 0.125 g |
| Sterile, pyrogen-free, pH 7 phosphate buffer, | q.s. to 25 ml |

EXAMPLE D

| Intramuscular injection | |
|---|---|
| Active Ingredient | 0.20 g |
| Benzyl Alcohol | 0.10 g |
| Glycofurol | 1.45 g |
| Water for Injection | q.s. to 3.00 ml |

The active ingredient was dissolved in the glycofurol. The benzyl alcohol was then added and dissolved, and water added to 3 ml. The mixture was then filtered through a sterile micropore filter and sealed in sterile 3 ml amber glass vials (type 1).

EXAMPLE E

| Syrup | |
|---|---|
| Active ingredient | 0.2500 g |
| Sorbitol Solution | 1.5000 g |
| Glycerol | 2.0000 g |
| Sodium Benzoate | 0.0050 g |
| Flavour, Peach 17.42.3169 | 0.0125 ml |
| Purified Water | q.s. to 5.0000 ml |

The active ingredient was dissolved in a mixture of the glycerol and most of the purified water. An aqueous solution of the sodium benzoate was then added to the solution, followed by addition of the sorbitol solution and finally the flavour. The volume was made up with purified water and mixed well.

EXAMPLE F

| Suppository | mg/suppository |
|---|---|
| Active Ingredient (631 m)* | 250 |
| Hard Fat, BP (Witepsol H15 - Dynamit Nobel) | 1770 |
| | 2020 |

*The active ingredient was used as a powder wherein at least 90% of the particles were of 631 m diameter or less.

One-fifth of the Witepsol H15 was melted in a steam-jacketed pan at 45° C. maximum. The active ingredient was sifted through a 200l m sieve and added to the molten base with mixing, using a silverson fitted with a cutting head, until a smooth dispersion was achieved. Maintaining the mixture at 45° C., the remaining Witepsol H15 was added to the suspension and stirred to ensure a homogeneous mix. The entire suspension was passed through a 250l m stainless steel screen and, with continuous stirring, was allowed to cool to 40° C. At a temperature of 38° C. to 40° C., 2.02 g of the mixture was filled into suitable, 2 ml plastic moulds. The suppositories were allowed to cool to room temperature.

EXAMPLE G

| Pessaries | mg/pessary |
| --- | --- |
| Active ingredient (631 m) | 250 |
| Anhydrate Dextrose | 380 |
| Potato Starch | 363 |
| Magnesium Stearate | 7 |
| | 1000 |

The above ingredients were mixed directly and pessaries prepared by direct compression of the resulting mixture.

Antiviral Testing

1. Anti-HCMV

Human cytomegalovirus (HCMV) is assayed in monolayers of MRC5 cells (human embryonic lung) in multiwell trays. Activity of compounds is determined in the plaque reduction assay, in which a cell monolayer is infected with a suspension of HCMV. A range of concentrations of the compound to be tested (of known molarity) is then incorporated into the carboxymethyl cellulose overlay. Plaque numbers of each concentration are expressed as percentage of the control and a dose-response curve is drawn. From this curve the 50% inhibitory concentration ($IC_{50}$) is estimated.

| Anti-HCMV Activity | |
| --- | --- |
| Compound | $IC_{50}$ ($\mu M$) |
| Ex. 4 | 1.9 |
| Ex. 13 | 1.0 |

2. Anti-HBV a. Overview

Anti-HBV activity of compounds of formula (I) and (I-1) was determined with a high-capacity assay for assessing efficacy. Supernatants from growing HBV-producing cells (HepG2 2.2.15, P5A cell line) in 96-well plates are applied to microtiter plate wells which have been coated with a specific monoclonal antibody to HBV surface antigen (HBsAg). Virus particles present in the supernatants bind to the antibody and remain immobilized while other debris is removed by washing. These virus particles are then denatured to release HBV DNA strands which are subsequently amplified by the polymerase chain reaction and detected with a colorimetric hybrid-capture assay. Quantitation is achieved through fitting of a standard curve to dilutions of a cell supernatant with known HBV DNA content. By comparing HBV DNA levels of untreated control cell supernatants with supernatants containing a compound of formula (I) or (I-1), a measure of anti-HBV effectiveness is obtained.

b. Immunoaffinity Capture of HBV

HBV producer cells, 2500 cells/well, were seeded in 96-well culture dishes in RPMI/10% fetal bovine serum/2 mM glutamine (RPMI/10/2:). Media were replenished on days 1, 3, 5, and 7 with dilutions of a compound of formula (I) or (I-1) in RPMI/10/2 to a final volume of 150 uL. Fifty uL of mouse monoclonal anti-HBsAG antibody (10 ug/mL in PBS) were added to each well of a round-bottom microtiter plate. After incubation overnight at 4° C., the solutions were aspirated and replaced with 100 uL of 0.1% BSA in PBS. Samples were incubated for 2 hours at 37° C. and washed three times with PBS/0/01% Tween-20 (PBS/T) using a Nunc Washer. Ten uL of 0.035% Tween 20 in PBS were then added to all wells by Pro/-Pette. Cell supernatants (25 uL) containing extracellular virion DNA were transferred into wells by Pro/Pette; the final Tween concentration is 0.01%. Twenty-five uL HBV standard media dilutions in RPMI/10/2 were added to 2 rows of wells to serve as an internal standard curve for quantitation, and the plates were sealed and incubated at 4° C. overnight. Samples were washed 5 times with PBS/T and 2 times with PBS, aspirating the last wash. Next, 25 uL of 0.09N NaOH/0.01% NP40 were added to each well by Pro/Pette, and the sample wells were sealed and incubated at 37° C. for 60 minutes. Samples were then neutralized with 25 uL of 0.09N HCl/100 mM tris (pH 8.3).

C. Polymerase Chain Reaction (PCR)

Polymerase chain reaction (Saiki, R. K. et al., Science, 239 (4839) 487–91 (1988)) was carried out on 5uL samples, using a Perkin Elmer PCR kit. PCR is performed in "MicroAmp tubes" in a final volume of 25 uL. Primers were chosen from conserved regions in the HBV genome, as determined by alignment of several sequences. One primer is biotinylated at the 5-prime end to facilitate hybrid-capture detection of the PCR products. All primers were purchased from Synthecell Corp., Rockville, Md. 20850.

d. Hybrid-Capture Detection of PCR Products

PCR products were detected with horse radish peroxidase-labeled oligonucleotide probes (Synthecell Corp., Rockville, Md. 20850), which hybridize to biotinylated strands of denatured PCR products directly in streptavidin-coated microtiter plate wells, using essentially the method of Holodiniy, M. et al., Bio Techniques, 12 (1) 37–39 (1992). Modifications included the use of 25λPCR reaction volumes and sodium hydroxide denaturation instead of heat. Simultaneous binding of the biotin moiety to the plate-bound streptavidin during the hybridization serves to "capture" the hybrids. Unbound labeled probes were washed away before colorimetric determination of the bound (hybridized) horse radish peroxidase. Quantities of HBV DNA present in the original samples were calculated by comparison with standards. These values were then compared to those from untreated cell cultures to determine the extent of anti-HBV activity.

$IC_{50}$ (the median inhibitory concentration) is the amount of compound which produces a 50 percent decrease in HBV DNA. The approximate $IC_{50}$ of the compounds of Examples 4, 13 and 69 are tabulated.

| Anti-HCMV Activity | |
| --- | --- |
| Compound | $IC_{50}$ ($\mu M$) |
| Ex. 4 | 0.74, 2.5 |
| Ex. 13 | 5.0 |
| Ex. 69 | 0.72, 1.3 | e. Selective Inhibition of T Cell Growth

The compounds of the invention were tested for inhibition of the growth of T cells (Molt 4) and B cells (IM9) by the method of Averett, D., Journal of Virological Methods, 23, (1989), 263–276.

| | $I_{50}$ $\mu M$ | |
| --- | --- | --- |
| Compound | Molt 4 cells | IM9 cells |
| Ex. 4 | 39 | 48 |
| Ex. 13 | 32 | 88 |

| Compound | I₅₀ μM Molt 4 cells | IM9 cells |
|---|---|---|
| Ex. 69 | 29 | 35 |

EXAMPLE 1

(±)-(1R*,2S*,3S*,5S*)-3-(Acetoxymethyl)-5-(4,5-dichloro-2-nitroanilino)-1,2-cyclopentanediyl diacetate (±)-(1R*,2S*,3R*,4R*)-tert-Butyl N-[2,3-dihydroxy-4-(hydroxymethyl)-1-cyclopentyl]carbamate (6.27 g, 25.1 mmol) and 1N hydrochloric acid (50 mL) were stirred overnight. The resulting clear solution was concentrated in vacuo and dried by evaporation of methanol and ethanol to give the hydrochloride of (±)-(1S*,2R*,3S*,5R*)-3-amino-5-(hydroxy-methyl)-1,2-cyclopentanediol as a solid foam (4.73 g). This solid foam was refluxed vigorously with triethylamine (7.5 g, 75 mmol), 1,2,4-trichloro-5-nitrobenzene (5.84 g, 25.0 mmol as 97%, Aldrich), and 2-methoxyethanol (75 mL) for 24 hours. The resulting black mixture was evaporated to dryness and the residue chromatographed on silica gel and product eluted with methanol:-chloroform/1:10 as a dark orange glass (6.9 g). Crystallization from ethanol-water gave orange powder (3.00 g) which was stirred in acetic anhydride (3.0 mL)-pyridine (20 mL) at ambient temperature overnight. Evaporation of volatiles, followed by crystallization from ethyl acetate-hexanes gave title compound as orange needles (2.82 g, 24%), m.p. 153°–156° C.; ¹H-NMR (DMSO-d₆) δ: 8.25 and 7.51 (both s, 1 each, C₆H₂), 8.07 (d, J=7.8 Hz, 1, NH), 5.23 and 5.09 (both m, 2,2 CHO), 4.3 (m, 1, CHN), 4.2–4.0 (m,2,CH₂O), 2.5–2.35 (m,2,2CH), 2.04, 2.03, 2.02 (all s, 9,3CH₃CO), 1.5–1.4 (m, 1, CH).

Anal. Calcd. for $C_{15}H_{20}N_2O_5Cl_2$: C, 46.67; H, 4.35; N, 6.05; Cl, 15.31. Found: C, 46.66; H, 4.37; N, 6.02; Cl, 15.38.

EXAMPLE 2

(±)-(1R*,2S*,3S*,5S*)-3-(Acetoxymethyl)-5-(5,6-dichloro-1H-benzimidazol-1-yl)-1,2-cyclopentanediyl diacetate (±)-(1R*,2S*,3S*,5S*)-3-(Acetoxymethyl)-5-(4,5-dichloro-2-nitroanilino)-1,2-cyclopentanediyl diacetate (2.75 g, 5.93 mmol) and Raney nickel (aqueous slurry, Aldrich, 300 mg wet) in isopropanol (250 mL) was shaken under hydrogen (40 psi) in a Parr shaker for 2.25 hours. Catalyst was filtered off with Celite and the filtrate acidified with 98% formic acid (5 mL) and concentrated to an orange oil. The oil was diluted with additional 98% formic acid (45 mL) and the resulting orange solution refluxed for 40 minutes. Volatiles were removed and the remaining dark oil dissolved in chloroform (100 mL). The chloroform solution was washed with saturated aqueous sodium bicarbonate (3×10 mL), dried (sodium sulfate), and evaporated to a foam which was chromatographed on silica gel. Title compound eluted with methanol:chloroform/3:97 as a white foam from ethyl acetate (2.26 g, 86%); ¹H-NMR (DMSO-d₆) δ: 8.57, 8.17, 7.97 (all s, 1 each, 3 benzimidazole CH), 5.6 (m, 1, CHO), 5.3–5.1 (m, 2, CHO and CHN), 4.35–4.15 (m, 2, CH₂O), 2.6–2.4 (m overlapping solvent, 2 CH), 2.10, 2.06, 1.92 (all s) overlapped by 2.0 (m, total 10,3CH₃CO and CH).

Anal. Calcd. for $C_{19}H_{20}N_2O_6Cl_2$: C, 51.49; H, 4.55; N, 6.32; Cl, 16.00. Found: C, 51.39; H, 4.58; N, 6.22; Cl, 16.07.

EXAMPLE 3

(±)-(1R*,2S*,3S*,5S*)-3-(Acetoxymethyl)-5-(2-bromo-5,6-dichloro-1H-benzimidazol-1-yl)-1,2-cyclopentanediyl diacetate (±)-(1R*,2S*,3S*,5S*)-3-(Acetoxymethyl)-5-(5,6-dichloro-1H-benzimidazol-1-yl)-1,2-cyclopentanediyl diacetate (1.32 g, 2.98 mmol) in dry N, N-dimethylformamide (6 mL) was heated to 60° C. Portions (ca. 1 mmol each) of N-bromosuccinimide (1.59 g, 8.93 mmol) were added over 5 hours. Heating was continued for an additional 4 hours. Volatiles were removed in vacuo and the residue chromatographed on silica gel. Title compound eluted with 1:1 hexane-ethylacetate as a tan powder (1.1 g, 69%), 1H-NMR identical with recrystalized sample. Such a sample was recrystallized from ethanol-water to a white powder, m.p. 156°–159° C.; ¹H-NMR (DMSO-d₆) δ: 8.34, 7.97 (both s, 1 each, 2 benzimidazole CH), 5.6 (m, 1, OCH), 5.3 (m, 1, OCH), 5.2–5.0 (m, 1, NCH), 4.4–4.2 (m, 2, OCH₂), 2.7–2.5 (m, 1, CH), 2.4–2.0 (m) overlapping 2.1 and 2.07 (both s, total 8, CH₂ and 2CH₃CO), 1.92 (s, 3, CH₃CO); mass spectrum (CI): 527 (6.6), 525 (45), 523 (100), 521 (65, M+1), 257 (48, M-B).

Anal. Calcd. for $C_{19}H_{19}N_2O_6$ BrCl₂: C, 43.71; H, 3.67; N, 5.37; total halogen as Br, 45.91. Found: C, 43.64; H, 3.63; N, 5.30; total halogen as Br, 45.77.

EXAMPLE 4

(±)-(1R*,2S*,3S*,5S*)-5-(2-Bromo-5,6-dichloro-1H-benzimidazol-1-yl)-3-(hydroxymethyl)-1,2-cyclopentanediol (±)-(1R*,2S*,3S*,5S*)-3-(Acetoxymethyl)-5-(2-bromo-5,6-dichloro-1H-benzimidazol-1-yl)-1,2-cyclopentanediyl diacetate (600 mg, 1.15 mmol) was added to a stirred mixture of sodium carbonate (122 mg) in water (2 mL)-ethanol (10 mL)-methanol (10 mL). After 2.5 hours at ambient temperature, the pH was adjusted to 7 with glacial acetic acid. Volatiles were removed in vacuo and the residue triturated with water (5 mL) and filtered to give white solid. Recrystallization of the solid from 1:1 ethanol-methanol gave title compound as a white powder (282 mg, 62%), m.p. 208°–211° C.; ¹H-NMR (DMSO-d₆) δ: 8.23, (s, 1, benzimidazole H7), 7.95 (s, benzimidazole H4), 5.13 (t, J=4.1 Hz, 1, CH₂OH), 5.03 (d, J=6.2 Hz, 1, OH), 5.0–4.85 (m, 1, H5), 4.71 (d, J=3.5 Hz, 1, OH), 4.55–4.45 (m, 1, H1), 3.85–3.80 (m, 1, H2), 3.7–3.6 and 3.55–3.45 (both m, 1 each, OCH₂), 2.2–1.95 (m, 3, H3 and H4); mass spectrum (CI): 395 (M+1).

Anal. Calcd. for $C_{13}H_{13}N_2O_3Cl_2Br$: C, 39.43; H, 3.31; N, 7.07; total halogen as Br, 60.52. Found: C, 39.50; H, 3.33; N, 7.02; total halogen as Br, 60.61.

EXAMPLE 5

(±)-(1R*,2S*,3S*,5S*)-3-(Acetoxymethyl)-5-(2,5,6-trichloro-1H-benzimidazol-1-yl)-1,2-cyclopentanediyl diacetate (±)-(1R*,2S*,3S*,5S*)-3-(Acetoxymethyl)-5-(5,6-dichloro-1H-benzimidazol-1-yl)-1,2-cyclopentanediyl diacetate (850 mg, 1.92 mmol) in dry N,N-dimethylformamide (5 mL) was maintained at 95° C. while N-chlorosuccinimide (760 mg) was added in portions over 3 hours. Heating was continued for a total of 6 hours. Volatiles were removed in vacuo and the residue chromatographed on silica gel. Title compound was eluted with ethyl acetate:hexanes/3:7 as a yellow solid (160 mg, 17%), $^1$H-NMR consistent with structure and almost identical with that of title compound of Example 3.

EXAMPLE 6

(±)-(1R*,2S*,3S*,5S*)-5-(2,5,6-trichloro-1H-benzimidazol-1-yl)-3-(hydroxymethyl)-1,2-cyclopentanediol (±)-(1R*,2S*,3S*,5S*)-3-(Acetoxymethyl)-5-(2,5,6-trichloro-1H-benzimidazol-1-yl)-1,2-cyclopentanediyl diacetate (160 mg, 3.40 mmol) was deblocked as in Example 4 to give, after elution from a silica gel compound, title compound as white powder, (36 mg, 31%), m.p. 206°–210° C.; $^1$H-NMR (DMSO-d$_6$) δ: 8.24 (s, 1, benzimidazole H7), 7.98 (s, 1, benzimidazole H4), 5.15–5.0 (m, 2, CH$_2$OH and OH), 5.0–4.8 (m, 1, H5), 4.74 (d, J=3.5 Hz, 1, OH), 4.55–4.50 (m, 1, H1), 3.9–3.75 (m, 1, H2), 3.7–3.4.(m, 2, OCH$_2$), 2.2–1.9 (m, 3, H3 and 2H4).

Anal. Calcd. for C$_{13}$H$_{13}$N$_2$O$_3$Cl$_3$: C, 44.41; H, 3.73; N, 7.97; Cl, 30.25. Found: C, 44.20; H, 3.81; N, 7.94; Cl, 30.08.

EXAMPLE 7

(1α,3β,4β)-(3,4-Dihydroxy-1-cyclopentyl)methyl benzoate

To a stirred, cooled (0° C.) solution of 4-hydroxymethylcyclopentene (J.-P. Depres and A. E. Green, *J. Org. Chem.* 1984, 49, 928–931, and references therein) (37.0 g, 276 mmol) in pyridine (450 mL) was added benzoylchloride (32.1 mL, 276 mmol) over 30 minutes. The resulting mixture was stirred at room temperature for 1.25 hours. Water (50 mL) was added and the volatiles removed in vacuo. The residual oil was dissolved in chloroform and the solution extracted with water and then dried over sodium sulfate. Evaporation of solvent gave (3-cyclopenten-1-yl)methylbenzoate as a yellow oil (53.94 g, 91%), sufficiently pure for use; $^1$H-NMR (DMSO-d$_6$) δ: 7.98, 7.67, 7.56 (m, 5, C$_6$H$_5$), 5.72 (s, 2, CH=CH), 4.19 (m, 2, OCH$_2$), 2.71 (m, 1, CH), 2.56–2.77 (m, overlapping solvent, 2CH), 2.21–2.14 (m, 2,2CH).

(3-Cyclopenten-1-yl)methyl benzoate (37.6 g, 0.161 mol) in acetone (200 mL) was added dropwise over 2 hours to a stirred solution of N-methylmorpholine-N-oxide (33.1 g, 60% in water, 0.169 mol), osmium tetroxide (2.5% in t-butanol, Aldrich, 3.0 mL), and acetone (200 mL) at ambient temperature. Stirring was continued for an additional 16 hours. Chloroform (500 mL) and water (150 mL) were added. The organic layer was separated, washed with cold 1N hydrochloric acid (2×150 mL) and then with saturated aqueous sodium bicarbonate (100 mL) and dried (MgSO$_4$). Volatiles were removed and the residual solid crystallized from toluene (200 mL) to give title compound as white crystals (26.9 g, 73%), m.p. 92°–94° C.; $^1$H-NMR (DMSO-d$_6$) δ: 7.96, 7.65, 7.56 (m, 5, C$_6$H$_5$), 4.38 (d, J=4.1 Hz, 2,2OH), 4.14 (d, J=6.6 Hz, 2, CH$_2$O), 3.90 (m, 2,2 OCH), 2.58 (m overlapping solvent, CH), 1.75 (m, 2,2CH), 1.55 (m, 2,2CH).

Anal. Calcd. for C$_{13}$H$_{16}$O$_4$: C, 66.09; H, 6.83. Found: C, 66.19; H, 6.86.

Concentration of mother liquors yielded 10.33 g of white solid which contained additional title compound contaminated by (±)-(1—, 3—, 4—)-(3,4-dihydroxy-1-cyclopentyl)methyl benzoate, ratio approximately 2:3 by $^1$H-NMR.

EXAMPLE 8

(3a-α,5α,6a-α)-(Tetrahydro-4H-cyclopenta-1,3,2-dioxathiol-5-yl)methyl benzoate S-oxide Thionyl chloride (6.04 g, 50.8 mmol) was added to a solution of (1β,3α, 4α)-(3,4-dihydroxy-1-cyclopentyl)-methyl benzoate (10.0 g, 42.3 mmol) in carbon tetrachloride (150 mL). The solution was refluxed for 1.5 hours. Solvent was evaporated to leave title compound as a thick oil sufficiently pure for use (see following example). Such a sample crystallized as a waxy solid from toluene, m.p. 48°–57° C.; $^1$H-NMR (DMSO-d$_6$) δ: 7.96, 7.66, 7.52 (m, 5, C$_6$H$_5$), 5.46 and 5.32 (both m, 1,2 OCH, due to ca 1:1 mixture of isomeric S-oxides), 4.28 (m, 2, OCH$_2$), 2.90 and 2.43 (both m, 1, CH of two isomeric S-oxides), 2.10 and 1.74 (both m, 4,4CH).

Anal. Calcd. for C$_{13}$H$_{14}$O$_5$S: C, 55.31; H, 5.00; S,11.36. Found: C, 55.41; H, 5.04; S, 11.30.

EXAMPLE 9

(3a-α,5α,6a-α)-(Tetrahydro-4H-cyclopenta-1,3,2-dioxathiol-5-yl)methyl benzoate S,S-dioxide (3a-α,5α,6a-α)-(Tetrahydro-4H-cyclopenta-1,3,2-dioxathiol-5-yl)methyl benzoate S-oxide (previous example, 42.3 mmol) was stirred in carbon tetrachloride (40 mL)-acetonitrile (40 mL)-water (60 mL) while sodium metaperiodate (8.98 g, 42.3 meq) and ruthenium trichloride (44 mg, 0.21 meq) were added. Additional sodium metaperiodate (179 mg) was added after 30 minutes to bring the reaction to completion as judged by TLC (silica gel, methanol:chloroform/1:19, visualized in iodine). After a total of 1.0 hour, methylene chloride (300 mL) was added. The organic layer was separated and the aqueous layer extracted with additional methylene chloride (300 mL). The combined organic layers were washed with saturated aqueous sodium bicarbonate (100 mL), then saturated aqueous sodium chloride (100 mL), dried (MgSO$_4$) and concentrated in vacuo to give title compound as white powder (12.37 g, 98%), m.p. 114°–119° C.; $^1$H-NMR (DMSO-d$_6$) δ: 8.02, 7.70, 7.55 (all m, 5, C$_6$H$_5$), 5.62 (m, 2, OCH), 4.34 (d, J=5.8 Hz, 2, OCH$_2$), 2.79–2.64 (m, 1, CH), 2.32–2.21 and 1.97–1.79 (m, 4,2 CH$_2$).

Anal. Calcd. for C$_{13}$H$_{14}$SO$_6$: C, 52.35; H, 4.73; S,10.75. Found: C, 52.32; H, 4.73; S, 10.69.

EXAMPLE 10

(±)-(1R*,2R*,4S*)-2-(5,6-Dichloro-1H-benzimidazol-1-yl)-4-(hydroxymethyl)cyclopentanol Sodium hydride (416 mg, 10.4 meq as 60% oil dispersion) was added to a solution of 5,6-dichlorobenzimidazole (L. B. Townsend and G. R. Revankar, *Chem.Rev.* 1970, 70, 389, and references therein) (1.50 g, 8.00 mmol) in dry N,N-dimethylformamide (35 mL). The mixture was stirred for 45 minutes at 25° C. (3a-α,5α,6a-α)-(tetrahydro-4H-cyclopenta-1,3,2-dioxathiol-5-yl)methyl benzoate S, S-dioxide (3.05 g, 10.2 mmol) was added in portions over 5 hours. Stirring was continued overnight at ambient temperature. Volatiles were removed in vacuo and the residual oil dissolved in 1,4-dioxane (130 mL)-water (10 mL) at reflux with 4M sulfuric acid (2.3 mL). After 10 minutes at reflux, the solution was basified with 5N sodium hydroxide, heated for an additional hour at 50° C., and then neutralized with additional acid. Evaporation of volatiles in vacuo gave residual solids which were extracted with chloroform to remove unreacted 5,6-dichlorobenzimidazole and then crystallized from ethanol-water to give title compound as white powder (2.09 g, 87%). Recrystallization of such a sample from ethanol-water gave title compound as white granules, m.p. 244°–245° C.; $^1$H-NMR (DMSO-$d_6$) δ: 8.47, 8.05, 7.93 (all s, 3, aryl CH), 5.19 (d, J=5.3 Hz, 1, CHOH), 4.71 (t, J=5.3 Hz, 1, CH$_2$OH), 4.6–4.5 (m, 1, NCH), 4.37–4.25 (m, 1, OCH), 3.41 (m, 2, OCH$_2$), 2.4–2.2 and 1.95–1.62 (m, 5,5CH).

Anal. Calcd. for $C_{13}H_{14}N_2O_2Cl_2 \cdot 0.02\ C_2H_5OH$: C, 51.85; H, 4.71; N, 9.27; Cl, 23.47. Found: C, 51.87; H, 4.74; N, 9.28; Cl, 23.60.

EXAMPLE 11

(±)-(1R*,2R*,4S*)-4-(Acetoxymethyl)-2-(5,6-dichloro-1H-benzimidazol-1-yl)cyclopentyl acetate (±)-(1R*,2R*,4S*)-2-(5,6-Dichloro-1H-benzimidazol-1-yl)-4-(hydroxymethyl)cyclo-pentanol (7.80 g, 25.8 mmol) was dissolved in pyridine (50 ml)-acetic anhydride (50 mL) and the solution stirred overnight. Volatiles were removed in vacuo and the residual oil partitioned between methylene chloride (150 mL) and saturated aqueous sodium bicarbonate (100 mL). The organic layer was dried (sodium sulfate) and evaporated to a glass (9.91 g, 99%); $^1$H-NMR (DMSO-$d_6$) δ: 8.58, 8.08, 7.96 (s, 3, aryl CH), 5.39–5.32 (m, 1, OCH), 5.09–5.04 (m, 1, NCH), 4.11 (d, J=6.6 Hz, 2, OCH$_2$), 2.59–2.50 (m overlapping solvent, CH), 2.41–2.35 (m, 1, CH), 2.17–1.86 (m overlapping 2.06 and 1.94, both s, total 9,3CH and 2CH$_3$CO).

Anal. Calcd. for $C_{17}H_{18}N_2O_2Cl_2 \cdot 0.1\ CH_2Cl_2$: C, 52.96; H, 4.70; N, 7.26, Cl, 18.55. Found: C, 52.86; H, 4.74; N, 7.25; Cl, 18.50.

EXAMPLE 12

(±)-(1R*,2R*,4S*)-4-(Acetoxymethyl)-2-(2-bromo-5,6-dichloro-1H-benzimidazol-1-yl)-cyclopentyl acetate N-Bromosuccinimide (4.54 g, 25.5 mmol) was added to a solution of (±)-(1R*,2R*,4S*)-4-(acetoxymethyl)-2-(5,6-dichloro-1H-benzimidazol-1-yl)cyclopentyl acetate (8.95 g, 23.2 mmol) in dry N,N-dimethylformamide (46 mL). The solution was maintained at ca. 70° C. (oil bath) for 5 hours. Volatiles were removed in vacuo and the residual orange syrup chromatographed on silica gel. Title compound was eluted with chloroform as a pale yellow solid (5.14 g, 48%), m.p. 122°–125° C.; $^1$H-NMR (DMSO-$d_6$) δ: 8.16 (s, 1, benzimidazole H7), 7.95 (s, 1, benzimidazole H4), 5.60–5.55 (m, 1, OCH), 5.12–5.03 (m, 1, NCH), 4.15 (d, J=6.3 Hz, 2, OCH$_2$), 2.66–2.60 (m, 1, CHCH$_2$), 2.29–2.14 (m, 3, CH), 2.06 (s, 3, CH$_3$CO), 1.93 (s, overlapped by m, 4, CH$_3$CO+CH); mass spectrum (CI): 469 (5.8), 467 (37.5), 465 (95), 463 (54, M+1), 199 (100, M-B).

Anal. Calcd. for $C_{17}H_{17}N_2Cl_2BrO_4$: C, 43.99; H, 3.69; N, 6.04; total halogen as Br, 51.65. Found: C, 44.06; H, 3.70; N, 5.97; total halogen as Br, 51.74.

EXAMPLE 13

(±)-(1R*,2R*,4S*)-2-(2-Bromo-5,6-dichloro-1H-benzimidazol-1-yl)-4-(hydroxymethyl)cyclo-pentanol (±)-(1R*,2R*,4S*)-4-(Acetoxymethyl)-2-(2-bromo-5,6-dichloro-1H-benzimidazol-1-yl)-cyclopentyl acetate (2.75 g, 5.92 mmol) was added to a stirred mixture of sodium carbonate (0.63 g) in water (11 mL)-ethanol (55 mL)-methanol (55 mL). After 2 hours at ambient temperature, the pH was adjusted to 7 with glacial acetic acid. Volatiles were removed in vacuo and the residue triturated with water (30 mL) and filtered to give white solid. Recrystallization of the solid from 1:1 ethanol-methanol gave title compound as white powder (1.62 g, 72%), m.p. 218°–220° C.; $^1$H-NMR (DMSO-$d_6$) δ: 8.18 (s, 1, benzimidazole H7), 7.97 (s, 1, benzimidazole H4), 5.20 (m, 1, OH), 4.95 (m, 1, OH), 4.80–4.60 (m, 2, OCH and NCH), 3.50–3.40 (m, 2, OCH$_2$), 2.45–2.20 (m, 1, CH), 2.20–1.60 (m, 4,4CH); mass spectrum (CI): 379 (M+1).

Anal. Calcd. for $C_{13}H_{13}N_2O_2Cl_2Br$: C, 41.08; H, 3.45; N, 7.37; total halogen as Br, 63.07. Found: C, 41.27; H, 3.49; N, 7.28; total halogen as Br, 62.88.

EXAMPLE 14

(±)-(1R*,2S*,3R*)-3-Azido-1,2-cyclopentanediol (±)-(1R*,2R*,3S*)-2,3-Epoxy-1-cyclopentanol (R. Steyn and H. Z. Sable, Tet 1969, 25, 3579) (36.2 g, 0.362 mol), sodium azide (47.1 g, 0.724 equiv), ammonium sulfate (23.9 g, 0.181 equiv), dioxane (200 mL) and water (180 mL) were slowly brought to reflux. After an initial exotherm had subsided, the solution was refluxed gently for 18 hours. Volatiles were removed and residual material extracted with absolute ethanol (250 mL). The ethanol was evaporated and the residual oil chromatographed on silica gel. Title compound eluted with methylene chloride as a pale yellow oil (41.0 g, 79%); $^1$H-NMR (DMSO-$d_6$) δ: 4.96 (d, J=6.4 Hz, 1, OH), 4.55 (d, J=3.9 Hz, 1, OH), 3.85–3.55 (m, 3,2 OCH and NCH), 2.1–1.75 and 1.55–1.2 (m, 4,2CH$_2$).

Anal. Calcd. for $C_5H_9N_3O_2$: C, 41.95; H, 6.34; N, 29.35. Found: C, 41.71; H, 6.36; N, 29.15. Continued elution of the column with methylene chloride gave 5.32 g of oil which consisted of additional title compound contaminated by ca. 50% of (±)-(1α,2β, 3α)-2-azido-1,3-cyclo-pentanediol.

EXAMPLE 15

(±)-(1R*,2S*,3R*)-3-Amino-1,2-cyclopentanediol (±)-(1R*,2S*,3R*)-3-Azido-1,2-cyclopentanediol (2.10 g, 14.7 mmol), 5% palladium on carbon (250 mg) and absolute ethanol (150 mL) were shaken on a Parr shaker under hydrogen (50 psi) for 3 hours. The catalyst was filtered (Celite) and solvent evaporated in vacuo to give title compound as white solid (1.65 g, 96%), m.p. 74°–76° C.

Anal. Calcd. for $C_5H_{11}NO_2$: C, 51.26; H, 9.46; N, 11.96. Found: C, 51.16; H, 9.52; N, 11.91.

EXAMPLE 16

(±)-(1R*,2S*,3R*)-3-(4,5-Dichloro-2-nitroanilino)-1,2-cyclopentanediol (±)-(1R*,2S*,3R*)-3-Amino-1,2-cyclopentanediol (7.10 g, 50.0 mmol), 1,2,4-trichloro-5-nitrobenzene (11.67 g, 50.0 mmol as 97%, Aldrich), triethylamine (10 mL) and t-butanol (50 mL) were refluxed under nitrogen for 7 hours. Volatiles were removed in vacuo and the black residue chromatographed on silica gel. Title compound was eluted with methanol:chloroform/1:24 as an orange solid (6.45 g, 42%). Crystallization of such a sample from ethanol-water gave title compound as yellow needles, m.p. 137°–140° C.; $^1$H-NMR (DMSO-$d_6$) δ: 8.26 and 7.49 (both s, 1 each, 2 aromatic CH), 8.06 (d, J=7.0 Hz, 1, NH), 5.04 (d, J=6.1 Hz, 1, OH), 4.65

(d, J=4.1 Hz, 1, OH), 4.0–3.7 (m, 3,2 OCH and NCH), 2.2–2.1, 2.0–1.8, 1.7–1.3 (all m, 4, 4 CH).

Anal. Calcd. for $C_{11}H_{12}N_2O_4Cl_2$: C, 43.02; H, 3.94; N, 9.12; Cl, 23.09. Found: C, 43.01; H, 3.92; N, 9.04; Cl, 23.15.

EXAMPLE 17

(±)-(1R*,2S*,3R*)-3-(2-Amino-5,6-dichloro-1H-benzimidazol-1-yl)-1,2-cyclopentanediol (±)-(1R*,2S*,3R*)-3-(4,5-Dichloro-2-nitroanilino)-1,2-cyclopentanediol (2.00 g, 6.51 mmol) in ethanol (100 mL) was shaken in a Parr shaker with Raney nickel (Aldrich, prewashed with water until neutral, ca. 1 tsp) under hydrogen (50 psi) for 1.5 hours, at which point uptake of hydrogen had ceased. TLC (silica gel, methanol:chloroform/1:10) shows one spot at lower $R_f$ than starting material. The catalyst was filtered off (Celite) and volatiles evaporated to leave a glass (2.0 g) which darkened readily in air. It was immediately dissolved in acetonitrile (20 mL) and cyanogen bromide (1M in acetonitrile, Aldrich, 1.4 mL, 7.0 mmol) was added and the solution stirred under nitrogen at ambient temperature overnight. The dark precipitate which formed dissolved on addition of water (20 mL). The purple solution was neutralized with 1N sodium hydroxide. The resulting precipitate was filtered off, washed with water, and crystallized form 95% ethanol (75 mL) to give gray-white powder (1.14 g, 58%), m.p. >250° C. dec; $^1$H-NMR (DMSO-$d_6$) δ: 7.37 and 7.32 (both s, 2,2 benzimidazole CH), 6.6 (br s, 2, NH$_2$), 4.81 (d, J=7.3 Hz, 1, OH), 4.73 (d, J=3.2 Hz, 1, OH), 4.7–4.5 (m, 1, NCH), 4.4 (m, 1, OCH), 2.4–1.6 (m, 4,4 CH).

Anal. Calcd. for $C_{12}H_{13}N_3O_2Cl_2$: C, 47.70; H, 4.34; N, 13.91; Cl, 23.47. Found: C, 47.80; H, 4.35; N, 13.83; Cl, 23.45.

EXAMPLE 18

(±)-(1R*,2S*,3R*)-3-(5,6-Dichloro-1H-benzimidazol-1-yl)-1,2-cyclopentanediyl diacet (±)-(1R*,2S*,3R*)-3-(4,5-Dichloro-2-nitroanilino)1,2-cyclopentanediol (2.00 g, 6.51 mmol) was stirred in acetic anhydride (1.8 mL)-pyridine (15 mL) at ambient temperature overnight. Volatiles were removed in vacuo. The residual oil was partitioned between saturated aqueous sodium bicarbonate and H$_2$O. The CHCl$_3$ layer was dried (Na$_2$SO$_4$) and solvent evaporated to a yellow solid (2.56 g). This diacetate was reduced with Raney nickel under hydrogen as in Example 17. Catalyst was filtered off and 98% formic acid (5 mL) was added to the ethanol filtrate. Volatiles were removed in vacuo and the residue refluxed in 98% formic acid (35 mL) for 30 minutes. The formic acid was evaporated and the residual oil partitioned between chloroform and excess saturated aqueous sodium bicarbonate. The chloroform layer was dried (Na$_2$SO$_4$) and concentrated to a brown oil. The oil was chromatographed on silica gel. Title compound eluted with 6–10% methanol-chloroform. Crystallization from ethanol-water gave title compound as white powder (1.77 g, 72%), m.p. 95°–97° C.; $^1$H-NMR (DMSO-$d_6$) δ: 8.56, 8.16, 7.96 (all s, 1 each, 3 benzimidazole CH), 5.6–5.5 (m, 1, OCH), 5.35–5.30 (m, 1, OCH), 5.15–5.05 (m, 1, NCH), 2.55–2.25 (m, overlapping solvent, 2 CH), 2.1–2.0 (m, overlapping s at 2.10, 4, CH and CH$_3$CO), 2.0–1.8 (m, overlapping s at 1.88, 4, CH and CH$_3$CO).

Anal. Calcd. for $C_{16}H_{16}N_2O_4Cl_2.0.45$ H$_2$O: C, 50.66; H, 4.49; N, 7.39; Cl, 18.69. Found: C, 50.73; H, 4.49; N, 7.36; Cl, 18.70.

EXAMPLE 19

(±)-(1R*,2S*,3R*)-3-(2-Bromo-5,6-dichloro-1H-benzimidazol-1-yl)-1,2-clyclopentanediol diacetate (±)-(1R*,2S*,3R*)-3-(Dichloro-1H-benzimidazol-1-yl)-1,2,-cyclopentanediyl diacetate (800 mg, 2.16 mmol) was brominated as in Example 3 and the title compound eluted from a silica gel column with ethyl acetate:hexanes/3:7 as a white powder (450 mg, 46%). Such a sample was resolidified from EtOAc-hexanes to give title compound as white powder, m.p. 140°–146° C.; $^1$H-NMR (DMSO-$d_6$) δ: 8.24 and 7.96 (both s, 1 each, H7 and H4), 5.8–5.7 (m, 1, OCH), 5.4–5.3 (m, 1, OCH), 5.2–5.1 (m, 1, NCH), 2.6–2.4 (m, overlapping solvent, CH), 2.4–2.15 (m, 2,2 CH), 2.11 (s, 3, CH$_3$CO), 1.95–1.80 (m overlapping s at 1.88, 4, CH and CH$_3$ CO); mass spectrum (CI): 455 (1.3), 453 (29), 451 (68), 449 (45, M+1).

Anal. Calcd. for $C_{16}H_{15}N_2O_4Cl_2Br$: C, 42.70; H, 3.36; N, 6.22; total halogen as Cl, 23.63. Found: C, 42.77; H, 3.41; N, 6.16; total halogen as Cl, 23.68.

EXAMPLE 20

(±)-(1R*,2S*,3R*)-3-(2-Bromo-5,6-dichloro-1H-benzimidazol-1-yl)-1,2-cyclopentanediol The diacetate of Example 19 (315 mg, 0.700 mmol) was deblocked as in Example 4, with chromatography of the crude product on silica gel. Title compound was eluted with methanol:chloroform/1:9 as white powder (180 mg, 74%), m.p. 169°–175° C.; $^1$H-NMR (DMSO-$d_6$) δ: 7.99 and 7.95 (both s, 2,2 benzimidazole CH), 5.08 (d, J=6.3 Hz, 1, OH), 5.0–4.85 (m, 1, NCH), 4.76 (d, J=3.0 Hz, 1, OH), 4.55–4.45 (m, 1, OCH), 4.05–3.95 (m, 1, OCH), 2.35–2.0 (m, 3, 3CH), 1.7–1.6 (m, 1, CH).

Anal. Calcd. for $C_{12}H_{11}N_2Cl_2O_2Br$: C, 39.20; H, 3.06; N, 7.62; total halogen as Cl, 28.93; Found: C, 38.99; H, 3.07; N, 7.49; total halogen as Cl, 29.16.

EXAMPLE 21

(−)-(1S,4R)-4-Amino-2-cyclopentene-1-carboxylic acid methanesulfonate

A solution of (−)-2-azabicyclo[2.2.1]hept-5-en-3-one (97.45 g, 0.8929 mol, Enzymatix Ltd.) in tetrahydrofuran (500 mL) was filtered and warmed to 35° C. A solution of methanesulfonic acid (63.7 mL, 0.9817 mol) in water (24.1 mL, 1.34 mol) was added over the course of 1.5 hours such that the ensuing exotherm did not exceed 45° C. The resulting slurry was heated at 60° C. for three hours, then allowed to cool to room temperature over the course of 15 hours. The slurry was filtered and the cake washed twice with anhydrous tetrahydrofuran (200 mL). An analytical sample of the wet cake was removed and dried to give the title compound as a white solid (1.264 g); m.p. 167°–169.2° C.; $^1$H-NMR (DMSO-$d_6$) δ: 12.6 (br s, 1H, CO$_2$H), 8.04 (br s, 3H, NH$_3^+$), 6.10 (dt, J=5.6, 2.0, 2.0 Hz, 1H, vinyl), 5.85 (dt, J=5.3, 2.3, 2.3 Hz, 1H, vinyl), 4.19 (br s, w½=20 Hz, 1H, allylic H), 3.61 (m, w½=22 Hz, 1H, allylic H), 2.53 (quintet, J=5.3 Hz (overlapping with DMSO peak), ½CH$_2$), 2.39 (s, 3H, CH$_3$SO$_3$H), 1.93 (dt, J=6.7, 6.7, 13.7 Hz, 1H, ½CH$_2$); $[\alpha]^{20}_{589}$ −83.8°, $[\alpha]^{20}_{578}$ −87.4°, $[\alpha]^{20}_{546}$ −101.2°, $[\alpha]^{20}_{436}$ −186.7°, $[\alpha]^{20}_{365}$ −316.2°

(c=1.42, methanol); CI-MS (CH₄): 128(M+1); EI-MS: 127(M).

Anal. Calcd. for C₇H₁₃NO5S: C, 37.66, H, 5.87; N, 6.27; S,14.36. Found: C, 37.65; H, 5.88; N, 6.30; S,14.44.

The remaining wet cake was used directly in the following example.

EXAMPLE 22

(−)-(1S,4R)-4-Amino-2-cyclopentene-1-methanol

The tetrahydrofuran-wet cake of (−)-(1S,4R)-4-amino-2-cyclopetene-1-carboxylic acid methanesulfonate prepared in Example 21 was suspended in dry tetrahydrofuran (400 mL) and transferred via cannula to a rapidly stirring solution of lithium aluminum hydride in tetrahydrofuran (1.0 molar, 1600 mL, 1.6 mol, Aldrich) cooled in an ice/acetone bath. The rate of transfer was limited to control the rate of gas evolution and to keep the temperature between 0° and 10° C. (total time of addition 1.5 hours). The resulting mixture was warmed to reflux over the course of two hours, then refluxed for 16 hours.

Approximately 1.6 L of solvent was removed by distillation, the resulting slurry was cooled in an ice-acetone bath, then treated with diethyl ether (dry, 1 L) and sodium fluoride (403.3 g, 9.605 mol, Aldrich). Water (86 mL, 4.8 mol) was added slowly at such a rate (three hours) that the temperature was kept below 5° C. and the hydrogen evolution was moderated. The resulting slurry was filtered and the cake washed with tetrahydrofuran (200 mL), then 7% water-tetrahydrofuran (500 mL). Quantitative HPLC analysis (see Example 23, below) of the filtrate showed it to contain 60.04 g of the title compound. The cake was reslurried in 7% water-tetrahydrofuran (1 L) for a half hour, filtered, and washed with 7% water-tetrahydrofuran (400 mL), then 10% water-tetrahydrofuran (300 mL). Quantitative HPLC analysis (see Example 23, below) of the filtrate showed it to contain 26.70 g of the title compound. The cake was reslurried in methanol (1 L) for 16 hours, filtered, and washed with methanol (500 mL). Quantitative HPLC analysis (see Example 23, below) of the filtrate showed it to contain 4.09 g of the title compound. The total yield of the title compound was thus 90.83 g, 0.8027 mol, or 90.5% of theoretical yield corrected for the analytical sample removed.

EXAMPLE 23

Analysis of (−)-(1S,4R)-4-Amino-2-cyclopentene-1-methanol and its enantiomer, (±)-(1R,4S)-4-amino-2-cyclopentene-1-methanol Samples of the title compounds were characterized by the method of Brückner, H., Wittner, R., and Godel, H., "Automated Enantioseparation of Amino Acids by Derivatization with o-Phthaldialdehyde and N-Acylated Cysteines", *J. Chrom.*, 476 (1989) 73–82. Using o-phthaldialdehyde and N-acetyl-L-cysteine as derivatizing reagents. The chromatographic separation used an Optima II ODS 100×4.5 mm, 3 μm column (III Supplies Co., Meriden, Conn.) and gradient elution at 0.9 mL/min using initially 100% sodium acetate buffer, 40 mM, pH 6.5, with a linear ramp to 18% acetonitrile over 15 minutes and a subsequent hold at 18% acetonitrile for 15 minutes. Detection was at 338 nm. Samples were dissolved in 0.1 molar borate buffer, pH 10.4. The identity and purity of the samples was established by comparison with authentic standards (see EP 434450 (Jun. 26, 1991)). The retention time of the (1S,RS) isomer was about 21 minutes. The retention time of the (1R,4S)-isomer was about 22 minutes.

EXAMPLE 24

(−)-(1R,4S)-tert-Butyl N-[4-hydroxymethyl)-2-cyclopenten-1-yl]carbamate

The first filtrate of Example 22 containing (−)-(1S,4R)-4-amino-2-cyclopentene-1-methanol was cooled in an ice-acetone bath and treated with di-tert-butyl dicarbonate (199.42 g, 0.9265 mol, Aldrich). The mixture was concentrated under vacuum to a volume of 300 mL, and added to the second filtrate of Example 22 that had meanwhile been cooled in an ice-acetone bath. The mixture was allowed to stir and warm to room temperature over the course of 18 hours, during which time gas evolved and a clear solution formed. This solution was combined with the last filtrate of Example 22 which had been evaporated under vacuum to a mixture of oil and solids. The resulting solution was evaporated under vacuum to an oil. The oil was partitioned between ethyl acetate (300 mL) and phosphate buffer (100 mL of 1.5 molar potassium dihydrogen phosphate adjusted to pH 7.0 with 50% sodium hydroxide-water). The phases were separated, the aqueous phase was reextracted twice with ethyl acetate (200 mL). The organic phases were dried over sodium sulfate and filtered through silica gel (50 g.). The solvent was removed under vacuum to give an oil (220.78 g), which was taken up in hexanes (300 mL). A minimum amount of ethyl acetate (about 50 mL) was added in order to dissolve the oil, and the solution was set to crystallize over the course of three days. The crystals were filtered off, washed with 20% ethyl acetate/hexanes, and dried by suction to a constant weight (156.1 g, 0.732 mol, 82.6% of theory) of the title compound; m.p. 73°–73.7° C.; ¹H-NMR (DMSO-d₆) δ: 6.72 (d, J=7.9 Hz, 1H, NH), 5.80 and 5.60 (two m, 2H, CH=CH), 4.59 (t, J=5.2 Hz, 1H, OH), 4.45 (m, 1H, CHN), 3.35 (m, overlapping H₂O, CH₂O), 2.60 (m, 1H, CH), 2.30 (m, 1H, ½CH₂), 1.40 (s, 9H, C(CH₃)₃), 1.2 (m, 1H, ½CH₂); $[\alpha]^{20}_{589}$−2.78°, $[\alpha]^{20}_{578}$−2.84°, $[\alpha]^{20}_{546}$−3.06°, $[\alpha]^{20}_{436}$−3.39°, $[\alpha]^{20}_{365}$−0.95° (c=5.07, methanol); CI-MS (CH₄) 214 (M+1); TLC (silica, 10% methanol-chloroform, iodine visualization), $R_f$=0.51.

Anal. Calcd. for C₁₁H₁₉O₃N: C, 61.95; H, 8.98, N, 6.57. Found: C, 61.87; H, 8.96; N, 6.59.

An additional 10.14 g of crystalline material was recovered from the mother liquor by crystallization and chromatography, bringing the total yield to 166.24 g (0.780 mol, 87.9% of theory from the lactam starting material of Example 21).

It was also found convenient to prepare the title compound directly from 2-azabicyclo[2.2.1]hept-5-en-3-one, either racemic or the (−) enantiomer, as follows. (−)-2-Azabicyclo[2.2.1]hept-5-en-3-one (6.00 g, 55.0 mmol) in anhydrous tetrahydrofuran (30 mL) was warmed to 34° C. and stirred while methanesulfonic acid (3.6 mL, 55 mmol) and water (0.99 mL, 55 mmol) were added dropwise over 10 minutes. An exotherm of 10° C. was observed within 5 minutes and a crystalline solid began to precipitate. The mixture was refluxed (oil bath at 74° C.) for 2.5 hours. The mixture was cooled to −10° C. and a solution of lithium aluminum hydride (1.0M in tetrahydrofuran, 100 mL) added. The first 15 mL was added over 10 minutes and an exotherm of 7° C. noted. The remaining 85 mL was added rapidly with no further exotherm noted. The mixture was brought to reflux over 30 minutes and reflux continued for 18 hours. The mixture was cooled to 25° C. and sodium fluoride (25.2 g, 0.600 mole) was added and, after stirring for 30 minutes water (5.3 mL) was added dropwise over 10 minutes to the cooled (0° C.) mixture. The mixture was stirred for 30 minutes at 25° C. and di-tert-butyl dicarbonate (12.6 mL, 55.0 mmol) was added. This mixture was stirred for 16 hours, filtered, and the cake triturated with ethyl acetate (2×50 mL). The combined filterate-wash was washed with water (20 mL), dried ($Na_2SO_4$), evaporated, and the residual syrup crystallized from ethyl acetate:hexanes/1:2 (30 mL) to give title compound as white crystals (10.32 g, 88%), identical in properties to the above-described sample.

EXAMPLE 25

(−)-(1R,2S,3R,4R)-tert-Butyl N-[2,3-dihydroxy-4-(hydroxymethyl)-1-cyclopentyl]-carbamate To a mixture of N-methyl morpholine-N-oxide (146.2 g, 60% in water, 0.749 mol) and osmium tetroxide (9.75 g, 2.5% in tert-butanol, 0.959 mmol) in acetone (1 L) stirring at −8° C. in an ice-acetone bath was added in one portion (−)-(1R,4S)-tert-butyl N-[4-hydroxymethyl)-2-cyclopenten-1-yl]carbamate (152.10 g, 0.7132 mol, from Example 24). The resulting mixture was allowed to warm to room temperature over 16 hours, during which time it became homogeneous. More osmium tetroxide was added (2.602 g, 0.256 mmol), and the solution was stirred at 20° C. for four hours, then 40° for two hours, at which time the reaction was judged complete by TLC (silica, 10% methanol-chloroform, visualization with iodine followed by vanillin char, starting material: $R_f$=0.51, products: $R_f$=0.22, (2S,3R)-isomer, and $R_f$=0.36, (2R,3S)-isomer). The ratio of (2S,3R)/(2R,3S) isomers was about 73:27 as judged by $^1$H-NMR and TLC. Water (75 mL) was added, followed by chloroform (2 L). The resulting two-phase mixture was cooled in an ice bath, and with very gentle agitation (to discourage phase mixing), anhydrous copper sulfate (457.8 g, Alfa) was added in several portions. The resulting slurry was allowed to stir at room temperature about 16 hours, then was filtered with filter aids (Celite 545 and 512). The cake was washed with tetrahydrofuran (6 L) until no more product eluted. The filtrate was evaporated under vacuum to a dark oil substantially free of N-methyl morpholine. The oil was filtered through silica gel (300 g), and eluted with tetrahydrofuran (3 L) until all of the product was eluted. The eluate was concentrated to 200 mL, and hexanes (about 300 mL) was added. Crystallization began spontaneously, and was allowed to continue at −5° C. for about 16 hours. The crystals were recovered by filtration, washed sparingly with 50% ethyl acetate-hexanes, and dried by suction to a constant weight (105.78 g, 0.428 mol, 60.0% of theoretical). Recrystallization from refluxing ethyl acetate (200 mL) provided the title compound as white crystals (93.85 g, 0.3795 mol, 53.2% of theoretical); m.p. 115.8°–117°; $^1$H-NMR (DMSO-$d_6$) δ: 6.71 (br d, J=7.4 Hz, 1H, NH), 4.52 (t, J=5.2 Hz, 1H, $CH_2OH$), 4.43 (d, J=5.1 Hz, 1H, CHOH), 4.31 (d, J=4.9 Hz, 1H, CHOH), 3.54–3.41 (overlapping multiplet, 3H, CHN and CHOH), 3.34 (m, overlapping with HOD, w½=20 Hz, $CH_2OH$), 1.99 (dt, J=12.5, 6.8, 6.8 Hz, 1H, $HOCH_2CH$), 1.85 (br. m, w½=30 Hz, 1H, ½$CH_2$), 1.39 (s, 9H, $C(CH_3)_3$), 0.98 (dt, J=12.4, 7.8, 7.8 Hz, 1H, ½$CH_2$); $[\alpha]^{20}_{589}$−8.08°, $[\alpha]^{20}_{578}$−8.57°, $[\alpha]^{20}_{546}$−9.95°, $[\alpha]^{20}_{436}$−18.22°, $[\alpha]^{20}_{365}$−29.36° (c=1.02, methanol); CI-MS ($CH_4$) 248(M+1).

Anal. Calcd. for $C_{11}H_{21}O_5N$: C, 53.43; H, 8.56; N, 5.66. Found: C, 53.45; H 8.58; N, 5.69.

A sample of the (−)-(2R,3S)-isomer (25.60 g) was obtained from the mother liquors by fractional crystallization from ethyl acetate; m.p. 106°–107.2° C.; $^1$H-NMR (DMSO-$d_6$) δ: 5.93 (br d, J=7.6 Hz, 1H, NH), 4.77 (d, J=4.9 Hz, 1H, CHOH), 4.58 (d, J=4.1 Hz, 1H, CHOH), 4.35 (br t, w½=15 Hz, 1H, $CH_2OH$), 3.89 (br s, w½=10 Hz, 1H, OCH), 3.73 (br s, 2H, OCH, NCH), 3.50 (br m, w½=20 Hz, 1H, ½$OCH_2$), 3.38 (br m, obscured by HOD, ½$OCH_2$), 1.90 (m, w½=24 Hz, 2H, $OCH_2CH$, ½$CH_2$), 1.38 (s, 9H, $C(CH_3)_3$), 1.27 (m, 1H, ½$CH_2$); $[\alpha]^{20}_{589}$−7.92°, $[\alpha]^{20}_{578}$−8.14°, $[\alpha]^{20}_{546}$−9.05°, $[\alpha]^{20}_{436}$−14.81°, $[\alpha]^{20}_{365}$−21.19° (c=1.36, methanol); CI-MS ($CH_4$), 248(M+1).

Anal. Calcd. for $C_{11}H_{21}O_5N$, 0.05 $H_2O$: C, 53.23; H, 8.57; N, 5.64. Found: C, 53.20; H, 8.55; N, 5.61.

In the same manner the racemate of Example 28 was converted to the racemate of title compound; m.p. 134°–136° C. (from ethyl acetate), 51%. $^1$H-NMR identical with that of (−)-enantiomer.

EXAMPLE 26

(±)-cis-4-Amino-2-cyclopentene-1-carboxylic acid, 4-toluenesulfonate

A 500 mL, three-neck flask with vertical joints was charged with (±)-2-azabicyclo[2.2.1]hept-5-en-3-one (48.66 g, 0.4459 mol, Cambridge), and equipped with a mechanical stirrer, thermometer with gas inlet adapter connected to the nitrogen supply, and a powder funnel. Tetrahydrofuran (200 mL, reagent grade) was added, and the stirrer started in order to dissolve the solid. An endotherm of 13° C. was noted. A gentle nitrogen sweep was applied from the inlet adapter out the powder funnel and 4-toluene sulfonic acid hydrate (93.52 g, 0.416 mol, 1.1 equv) was added, along with a small amount of the title compound as seed. The powder funnel was replaced by a reflux condenser, and the flask was immersed in an oil bath preequilibrated to 35° C. Within 10 minutes, crystallization began, followed by an exotherm peaking at 60° C. in another 15 minutes. After the exotherm peaked, the bath was reset to 60°–65° C., and the reaction mixture was heated two hours at 60°–65° C. (internal), until a TLC of the supernatant liquid (silica, ethyl acetate eluent, iodine visualization) shows the absence of starting lactam against an authentic spot. The mixture was then cooled in an ice bath to 5° C. A glass tube with a fritted end was connected via flexible tubing to a filter flask, in turn connected to a vacuum source. The condenser was removed from the flask containing the slurry, the stirrer was stopped, and with a nitrogen sweep from the gas inlet, the fritted end of the stick was pushed to the bottom of the flask under the agitator. Vacuum was applied until the liquid was completely removed, the solids were reslurried in dry tetrahydrofuran (100 mL), and the filtration operation was repeated. The resulting white solids were reslurried in dry tetrahydrofuran (200 mL), and the open neck was capped with a septum. The resulting slurry of the title compound was used directly in the following Example; an analytical sample was prepared similarly, except that it was dried first by suction then by the application of vacuum; m.p. 191°–193° C.; $^1$H-NMR (DMSO-$d_6$), δ: 12.62 (br s, 1H, $CO_2H$), 7.93 (br s, 3H, $NH_3^+$), 7.47 and 7.11 (dd, 8.0

Hz, 2H each, Ar-H), 6.11 (dt, J=5.7, 1.9, 1.9, Hz, 1H, vinyl), 5.82 (dr, J=5.7, 2.8, 2.8 Hz, 1H vinyl), 4.20 (br m, w½=21 Hz, 1H, allylic H), 3.61 (br tt?, w½=21 Hz, 1H, allylic), 2.29 (s, 3H, CH$_3$), 2.50 (dt?, J=5.8, 5.8, 11.5 Hz, (overlapping DMSO peak), ½CH$_2$), 1.92 (dt, J=6.7, 6.7, 13.4 Hz, 1H, ½CH$_2$).

Anal. Calcd. for $C_{13}H_{17}O_5N_5$: C, 52.16; H, 5.72; N, 4.68; S, 10.71. Found: C, 52.16; H, 5.76; N, 4.66; S, 10.62.

EXAMPLE 27

(±)-cis-4-Amino-2-cyclopentene-1-methanol

A dry, 2 L, three-neck flask was equipped with a mechanical stirrer, thermometer with gas inlet adapter connected to the nitrogen supply, and septum. The flask was purged with nitrogen, immersed in an ice-acetone bath, and lithium aluminum hydride solution in tetrahydrofuran (1.0 molar, 800 mL, 0.80 mol, Aldrich) was added via cannula. Dry tetrahydrofuran (2×15 mL) was used to rinse in the lithium aluminum hydride solution. When the solution had cooled to 0° C., the slurry of (±)-cis-4-amino-2-cyclopentene-1-carboxylic acid 4-toluenesulfonate salt in tetrahydrofuran prepared in the previous Example was cannulated in with good stirring, at such a rate as to keep the temperature less than 10° C. and moderate the hydrogen evolution (about one hour). The flask was rinsed with dry tetrahydrofuran (2×15 mL), and the septum was replaced with a reflux condenser. The resulting clear, light amber solution was slowly warmed to a gentle reflux over the course of two hours, at which point it became cloudy. After refluxing overnight (16 hours), the heating bath was dropped, sodium fluoride (136.3 g, 3.25 mol, reagent grade powder) was added, and the condenser reset for downward distillation. The mixture was distilled to a thin slurry (700 mL of distillate collected), then cooled in an ice bath. Diethyl ether (dry, 500 mL) was added, and the condenser was replaced by an addition funnel containing water (43 mL, 2.4 mol). The water was added very slowly (two hours), with care taken to control the rate of hydrogen evolution and maintain the temperature at 10°±5° C. Meanwhile, water (54 mL) was added to the above recovered distillate, and sufficient additional tetrahydrofuran was added to bring the total volume to 900 mL (6% H$_2$O). The reaction mixture was filtered by suction, and the cake displace-washed with tetrahydrofuran (100 mL). Part of the 6% water-tetrahydrofuran solution (300 mL) was used to slurry-wash the cake, which was then returned to the reaction flask. The cake was triturated (25 minutes) in 6% water-tetrahydrofuran (400 mL), filtered, and displace-washed with 6% water-tetrahydrofuran (200 mL). The combined filtrates were concentrated to a pale yellow oil under vacuum (44.07 g, 67.8% by HPLC, see Example 3). This oil, containing pure title compound, water, and a trace of tosylate salt, darkens rapidly under ambient conditions. It was immediately reacted to form the N-BOC derivative, a stable, crystalline solid, (see the following Example). The filter cake was returned to the flask and triturated in methanol (800 mL) for 48 hours. The resulting slurry was filtered under a rubber dam, and the cake was washed with methanol (200 mL). The filtrate was concentrated under vacuum to a yellow solid (56.80 g, 20.9% yield by HPLC; total overall yield 88.7%). This extract was also taken to the N-BOC derivative (see the following Example).

EXAMPLE 28

(±)-cis-tert-Butyl N-[4-(hydroxymethyl)-2-cyclopenten-1-yl]carbamate

The first extract of the previous example containing (±)-cis-4-Amino-2-cyclopentene-1-methanol (0.4459 mol) was dissolved in 2:1 1,4-dioxane-water (1.2 L). Sodium bicarbonate (48.69 g, 0.580 mol) was added, the mixture was cooled in an ice-water bath and di-tert-butyldicarbonate (110.25 g, 0.490 mol, Aldrich 97%) was added in one portion with rapid stirring. The resulting mixture was warmed to room temperature over the course of one hour, then was concentrated under vacuum to a volume of about 400 mL. The slurry was taken up in chloroform (300 mL), the phases were separated, and the aqueous (upper) phase was reextracted with chloroform (five portions of 300 mL each) until no product was observed in the extract by TLC (silica, 10% methanol-chloroform, iodine visualization, R$_f$=0.51). The combined organic phases were dried over sodium sulfate, filtered and concentrated under vacuum to give the title compound as an oil. The final extract of the previous example was reacted similarly, and the crude title compound thus obtained was combined with the above portion, the combined material was taken up in hexanes and evaporated under vacuum to remove residual chloroform. The oil then crystallized spontaneously. It was triturated in cold hexanes and filtered to give the crude title compound as a crystalline solid, which was dried by suction to a constant weight (79.98 g, 0.3750 mol). Recrystallization from boiling ethyl acetate (70 mL) and hexanes (300 mL) gave the title compound as a off-white, crystalline solid (73.43 g, 0.3443 mol); m.p. 54°-55.5° C.; $^1$H-NMR (DMSO-d$_6$) δ: 6.72 (d, J=7.9 Hz, 1H, NH), 5.80 and 5.60 (two m, 2H, CH=CH), 4.59 (t, J=5.2 Hz, 1H, OH), 4.45 (m, 1H, CHN), 3.35 (m, overlapping H$_2$O, CH$_2$O), 2.60 (m, 1H, CH), 2.30 (m, 1H, ½CH$_2$), 1.40 (s, 9H, C(CH$_3$)$_3$), 1.2 (m, 1H, ½CH$_2$).

Anal Calcd. for $C_{11}H_{19}NO_3$: C, 61.94; H, 8.98; N, 6.57. Found: C, 62.00; H, 8.99; N, 6.55.

The mother liquors were combined, chromatographed on silica gel (700 g, 30% ethyl acetate-hexanes and 5% methanol-chloroform), and crystallized as above to give a second portion of the title compound (10.49 g, 0.0492 mmol). The total yield was thus 0.3935 mol, or 88.9% of theoretical from the starting (±)-2-azabicyclo[2.2.1]hept-5-en-3-one (corrected for aliquots taken).

EXAMPLE 29

(±)-cis-4-Amino-2-cyclopentene-1-methanol

By the method of Examples 26 and 27, but on about twice the scale (97.40 g, 0.8924 mol of (±)-2-azabicyclo[2.2.1]hept-5-en-3-one) the title compound was obtained as extracts containing the title compound (0.7926 mol, 88.8% of theoretical, allowing for aliquots removed, as determined by the method of Example 23).

EXAMPLE 30

(±)-cis-tert-Butyl N-(4-[hydroxymethyl)-2-cyclopenten-1-yl]carbamate

The combined tetrahydrofuran extracts from the preceding Example were concentrated under vacuum to 1031 g, cooled in an ice-water bath, and a mixture of sodium bicarbonate (97.46 g, 1.16 mol) in water (500 mL) was added. This was followed by di-tert-butyl dicarbonate (204.5 g), 0.9501 mol). The mixture was stirred at 5° C. for two days. The methanol extracts from the preceding Example were evaporated to an oily solid (136.64 g), which was added to the mixture. After warming to room temperature, the organic solvents were evaporated under vacuum, and the resulting slurry was extracted with hexanes, three portions of methylene chloride, then hexanes again (200 mL each). The organic extracts were evaporated to an oil, which was crystallized from hexanes (about 300 mL), giving the title compound (154.15 g, 0.7229 mol), identical to the product of Example 28. Additional product was obtained by chromatography of the mother liquors (10.5 g, 0.0491 mol, 86.6% of theoretical from the starting lactam, allowing for aliquots removed).

EXAMPLE 31

(±)-cis-4-Amino-2-cyclopentene-1-carboxylic acid, methanesulfonate

Beginning with (±)-2-azabicyclo[2.2.1]hept-5-en-3-one (5.111 g, 46.83 mmol, Cambridge), by the method of Example 31, was prepared the title compound (10.268 g, 45.99 mmol, 98.2%); m.p. 137°–139° C.; $^1$H-NMR (DMSO-d$_6$) δ: 12.6 (br s, 1H, CO$_2$H), 8.04 (br s, 3H, NH$_3$+), 6.10 (dt, J=5.6, 2.0, 2.0 Hz, 1H, vinyl), 5.85 (dt, J=5.3, 2.3, 2.3 Hz, 1H, vinyl), 4.19 (br s., w½=20 Hz, 1H, allylic H), 3.61 (m, w½=22 Hz, 1H, allylic H). 2.53 (quintet, J=5.3 Hz (overlapping with DMSO peak), ½CH$_2$), 2.39 (s, 3H, CH$_3$SO$_3$H), 1.93 (dt, J=6.7, 6.7, 13.7 Hz, 1H, ½CH$_2$);CI-MS (CH$_4$): 128(M+1); EI-MS: 127(M).

Anal. Calcd. for C$_7$H$_{13}$NO$_5$S: C, 37.66; H, 5.87; N, 6.27; S,14.36 Found: C, 37.60; H, 5.85; N, 6.25; S,14.30

EXAMPLE 32

(±)-cis-4-Amino-2-cyclopentene-1-carboxylic acid, 4-toluenesulfonate

To a solution containing a catalytic amount of 4-toluene sulfonic acid (10 mg) in 30% aqueous hydrogen peroxide (0.30 mL, 2.7 mmol) was added 3-tosyl-2-azabicyclo[2.2.1]hepta-2,5-diene (369 mg, 1.49 mmol), prepared by the method of J. C. Jagt and A. M van Leusen, J. Org. Chem. 1974, 39, 564–566, in portions, with rapid stirring. A large exotherm is noted, stabilizing at 75° C. during the last half of the addition. After stirring 70° C. for 40 minutes, the mixture was repeatedly diluted with water (6 mL total) and filtered until a clear solution resulted. The solution was evaporated to an oil which crystallized (349 mg). This was triturated in tetrahydrofuran, filtered, and dried under vacuum to give the title compound (202 mg, 45.2% of theoretical), $^1$H-NMR spectrum identical to the product of Example 26.

EXAMPLE 33

(±)-cis-[4-(4,5-Dichloro-2-nitroanilino)-2-cyclopenten-1-yl]methanol (±)-cis-tert-Butyl N-[4-(hydroxymethyl)-2-cyclopenten-1-yl]carbamate (50.0 g, 0.230 mole) was stirred in 25% trifluoroacetic acid in methylene chloride (1.5 L) at 0° C. for 1.0 hour. Evaporation of volatiles left the trifluroacetic acid salt of the amine described in Example 27 as a dark oil. To this oil were added t-butanol (350 mL), potassium carbonate (65 g), and 1,2,4-trichloro-5-nitrobenzene (Aldrich, 54.7 g, 0.230 mole as 97%). The resulting mixture was refluxed with vigorous stirring for 3 days. Volatiles were removed under vacuum and the residue triturated with methanol. The methanol-soluble material was chromatographed on silica gel. Crude product was eluted with 2% methanol-chloroform to give orange solid (38.0 g). Crystallization from ethyl acetate-hexanes gave title compound as orange crystals (34.0 g, 49%), m.p. 96°–98° C.; $^1$H-NMR(DMSO-d$_6$) and mass spectrum(CI) consistent with structure and identical with samples of chiral enantiomers described in Examples 53 and 64.

Anal. Calcd. for C$_{12}$H$_{12}$N$_2$Cl$_2$O$_3$: C, 47.55; H, 3.99: N, 9.24 Cl, 23.39. Found: C, 47.75; H, 4.10; N, 9.20; Cl, 23.52.

Continued elution of the column gave further fractions containing title compound with minor low R$_f$ impurities. These fractions were combined with the mother liquor from the above crystallization and recrystallized from ethyl acetate-hexanes to give additional orange solid (16.7 g) having identical 1H-NMR spectrum and bringing the total yield to 73%.

EXAMPLE 34

(±)-cis-[4-(5,6-Dichloro-1H-benzimidazol-1-yl)-2-cyclopenten-1-yl]methanol (±)-cis-[4-(4,5-Dichloro-2-nitroanilino)-2-cyclopenten-1-yl]methanol (5.00 g, 16.5 mmol) in ethanol (100 mL)-water (35 mL) was heated while iron powder (325 mesh, 99.9%, Aldrich, 9.2 g, 0.165 equiv) and iron(II) sulfate heptahydrate (Aldrich, 98+%, 2.3 g, 8.2 mequiv) were added. The mixture was refluxed 1.75 hours. Solids were filtered off and the ethanol filtrate-wash concentrated to an oil. Triethylorthoformate (75 mL) and methanesulfonic acid (0.05 mL) were added to the oil and the resulting solution stirred at ambient temperature for 18 hours. Concentration in vacuo left an oil which was redissolved in 1N hydrochloric acid (25 mL)-dioxane(5 mL). After 3 hours, the pH was adjusted to 7 with 1N sodium hydroxide and the solution extracted with chloroform (3×50 mL). The contents of the dried (sodium sulfate) chloroform solution was chromatographed on silica gel. Title compound was eluted with 5% methanol-chloroform and crystallized from ethyl acetate-hexanes to give white crystals (3.85 g, 82%), m.p. 166°–169° C.; $^1$H-NMR(DMSO-d$_6$) and mass spectrum(CI) consistent with structure.

Anal. Calcd. for C$_{13}$H$_{12}$N$_2$Cl$_2$O: C, 55.14; H, 4.27: N, 9.89; Cl, 25.04. Found: C, 55.20; H, 4.32; N, 9.84; Cl, 24.94.

EXAMPLE 35

(±)-cis-[4-(2-Bromo-5,6-dichloro-1H-benzimidazol-1-yl)-2-cyclopenten-1-yl]methanol (±)-cis-[4-(5,6-Dichloro-1H-benzimidazol-1-yl)-2-cyclopenten-1-yl]methanol (1.55 g, 5.47 mmol) was acetylated in pyridine (17 mL) with acetic anhydride (0.6 mL) at ambient temperature for 2 days. Volatiles were removed in vacuo and the residual oil partitioned between chloroform and aqueous sodium bicarbonate. The chloroform solution was dried (sodium sulfate) and concentrated to dryness. The residue was dissolved in dry dioxane (10 mL) and the solution brought to reflux. N-bromosuccinimide (930 mg, 5.23 mmol) was added all at once. The dark solution was cooled after 4 minutes of reflux. Volatiles were evaporated in vacuo and the residue was chromatographed on silica gel. Elution with 2–5% methanol-chloroform gave fractions containing starting material (1.05 g) followed by fractions containing title compound as a dark oil (0.28 g). The recovered starting material was again treated with N-bromosuccinimide and the crude product chromatographed. All product-containing fractions were combined and rechromatographed on silica gel with elution by hexanes-ethyl acetate to give the acetate of title compound as a yellow oil (0.62 g). Deacetylation was carried out as in Example 4. Volatiles were evaporated in vacuo from the neutralized solution and the residue was chromatograped on silica gel. Elution with 2% methanol-chloroform gave (±)-cis-[4-(2-bromo-5,6-dichloro-1H-benzimidazol-1-yl)-2-cyclopenten-1-yl]methanol as off-white powder (293 mg, 15%), after resolidification from hexanes-ethyl acetate, m.p. 126°–128.5° C.; $^1$H-NMR(DMSO-d$_6$) δ: 8.09 and 7.95 (both s, 1 each, aromatic CH), 6.24–6.20 and 5.98–5.94 (both m, 2, CH=CH), 5.81–5.76 (2 m, 1 each, CH$_2$O), 4.96 (t, J=4.9 Hz, 1, OH), 3.02–2.95 (m, 1, CH), 2.67–2.51 (m overlapping solvent, ½CH$_2$), 2.0–1.8 (m, 1, ½CH$_2$); mass spectrum (CI) consistent with structure.

Anal. Calcd. for C$_{13}$H$_{11}$N$_2$BrCl$_2$O: C, 43.13; H, 3.06; N, 7.74; total halogen as Cl, 29.38. Found: C, 43.20; H, 3.07; N, 7.71; total halogen as Cl, 29.35.

EXAMPLE 36

(±)-cis-3-(5,6-Dichloro-1H-benzimidazol-1-yl)-1-cyclopentanemethanol

A mixture of (±)-cis-[4-(4,5-dichloro-2-nitroanilino)-2-cyclopenten-1-yl]methanol (5.00 g, 16.5 mmol) and Raney nickel (Aldrich, slurry in water, 500 mg wet) in n-propanol (250 mL) was shaken under hydrogen (50 psi) on a Parr shaker for 2 hours. The catalyst was filtered off, solvent evaporated in vacuo, and the residue dissolved in triethylorthoformate(300 mL)-methanesulfonic acid (200 mg). After 18 hours, the solution was concentrated to a syrup which was dissolved in 1N hydrochloric acid (40 mL) and stirred at ambient temperature overnight. The pH was adjusted to 7 with 1N sodium hydroxide and the solution extracted with chloroform (3×50 mL). The contents of the dried (sodium sulfate) chloroform solution was chromatographed on silica gel. Title compound was eluted with 5% methanol-chloroform as a colorless oil which solidified from ethyl acetate-hexanes to give white powder (3.98 g, 85%). m.p. 142°–145° C.; $^1$H-NMR(DMSO-d$_6$) and mass spectrum(CI) consistent with structure.

Anal. Calcd. for C$_{13}$H$_{14}$N$_2$Cl$_2$O: C, 54.75; H, 4.95:N, 9.82; Cl, 24.86. Found: C, 54.88; H, 4.99; N, 9.70; Cl, 24.74.

EXAMPLE 37

(±)-cis-3-(2-Bromo-5,6-dichloro-1H-benzimidazol-1-yl)-1-cyclopentanemethanol (±)-cis-3-(5,6-Dichloro-1H-benzimidazol-1-yl)-1-cyclopentanemethanol (3.65 g, 12.8 mmol) was acetylated in pyridine (40 mL)-acetic anhydride (2 mL) at ambient temperature overnight. Volatiles were evaporated and the residue partitioned between chloroform and saturated aqueous sodium carbonate. The chloroform layer was dried (sodium sulfate) and evaporated to a glass which was reacted with N-bromosuccinimide as in Example 3. The crude bromination product was chromatographed on silica gel and the acetate of title compound was eluted with 5% methanol-chloroform as an off-white powder (2.8 g, 55%); $^1$H-NMR(DMSO-d$_6$) and mass spectrum(CI) consistent with structure. This powder (2.00 g, 4.92 mmol) was deacetylated as in Example 4 to give colorless solid foam, after elution from a silica gel column with 2–3% methanol-chloroform. Crystallization from ethyl acetate-hexanes gave (±)-cis-3-(2-bromo-5,6-dichloro-1H-benzimidazol-1-yl)-1-cyclopentanemethanol as off-white crystals (1.08 g, 60%), m.p. 111°–112° C.; $^1$H-NMR(DMSO-d$_6$) δ: 8.08 and 7.96 (both s, 1 each, 2 aromatic CH), 5.06–5.01 (m, 1, NCH), 4.79 (t, J=5.1 Hz, 1,)H), 3.56–3.51 (m, 2, CH$_2$OH), 2.28–2.05 (m, 5,2 CH$_2$ and CH); mass spectrum(CI): 367(54), 365(100), 363(71, M+I).

Anal. Calcd. for C$_{13}$H$_{13}$N$_2$BrCl$_2$O: C, 42.89; H, 3.60:N, 7.69; total halogen as Br, 65.84, as Cl, 29.21. Found: C, 42.94; H, 3.63; N, 7.62; total halogen as Br, 65.75, as Cl, 29.17.

EXAMPLE 38

(±)-(1R*,2S*,3S*,5S*)-3-(Acetoxymethyl)-5-(4,5-dichloro-2-nitroanilino)-1,2-cyclopentanediyl diacetate and (±)(1R*,2S*,3R*,5R*)-3-(acetoxymethyl)-5-(4,5-dichloro-2-nitroanilino)-1,2-cyclopentanediyl diacetate To a solution of (±)-cis-[4-(4,5-dichloro-2-nitroanilino)-2-cyclopenten-1-yl]methanol (20.0 g, 66.0 mmol) and N-methylmorpholine N-oxide (Aldrich, 60% aqueous solution, 12.0 mL, 69 mmol) in acetone (280 mL) was added osmium tetroxide (2.5% in t-butyl alcohol, Aldrich, 1.24 mL). After stirring at ambient temperature for 18 hours, volatiles were removed in vacuo and the residue stirred with pyridine (200 mL)-acetic anhydride (40 mL) for an additional 18 hours. The solution was concentrated to a thick red oil which was partitioned between saturated aqueous sodium carbonate and chloroform. The chloroform layer was dried (sodium sulfate) and then concentrated to an oil in vacuo. A mixture of the isomeric title compounds was eluted from a silica gel column with 2% methanol-chloroform and crystallized from ethyl acetate-hexanes (with seeding by crystals of the (1R*,2S*)-isomer prepared by the method of Example 1) to give (±)-(1R*,2S*,3S*,5S*)-3-(acetoxymethyl)-5-(4,5-dichloro-2-nitroanilino)-1,2-cyclopentanediyl diacetate as orange crystals (17.4 g, 57%), m.p. 154°–156° C.; $^1$H-NMR(DMSO-d$_6$) identical to that of the sample described in Example 1.

Continued crystallization of the mother liquor contents from ethyl acetate-hexanes gave (±)(1R*,2S*,3R*,5R*)-3-(acetoxymethyl)-5-(4,5-dichloroo2-nitroanilino)-1,2-cyclopentanediyl diacetate as orange crystals (8.82 g, 29%), m.p. 105°–107° C.; $^1$H-NMR(DMSO-d$_6$) identical with that of the chiral sample described in Example 61.

Anal. Calcd. for C$_{18}$H$_{20}$N$_2$Cl$_2$O$_8$: C, 46.67; H, 4.35; N, 6.05; Cl, 15.31. Found: C, 46.50; H, 4.33; N, 5.96; Cl, 15.23.

EXAMPLE 39

(±)(1R*,2S*,3R*,5R*)-3-(Acetoxymethyl)-5-(2-bromo-5,6-dichloro-1H-benzimidazol-1-yl)-1,2-cyclopentanediyl diacetate (±)(1R*,2S*,3R*,5R*)-3-(Acetoxymethyl)-5-(4,5-dichloro-2-nitroanilino)-1,2-diacetate (5.00 g, 10.8 mmol) was stirred in ammonia/methanol (ca. 2N, 100 mL) at ambient temperature for 18 hours. Evaporation of volatiles in vacuo left residual orange solid (±)-(1R*,2S*,3R*,5R*)-5-(4,5-dichloro-2-nitroanilino)-3-(hydroxymethyl)-1,2-cyclopentanediol having an identical $R_f$ on silica gel TLC plates to that of the chiral sample described in Example 54. This solid was reduced with Raney nickel/hydrogen(45 psi) in isopropanol (200 mL). Catalyst was filtered off with Celite. The filtrate-wash was evaporated to dryness in vacuo. The residue was refluxed in formic acid (96%, 50 mL) for one hour, as described in Example 2. The oil remaining on evaporation of the formic acid was dissolved in methanol. The pH was adjusted to 13 with aqueous 5N sodium hydroxide and the solution was stirred at ambient temperature for one hour to hydrolyze formate esters. The pH was adjusted to 7 with 1N hydrochloric acid and volatiles removed by evaporation in vacuo. Pyridine (100 mL) and acetic anhydride (4 mL) were added to the residue and the mixture stirred at ambient temperature overnight. Evaporation of volatiles in vacuo followed by chromatography on silica gel with 1% methanol-chloroform gave (±)-(1R*,2S*,3R*,5R*)-3-(acetoxymethyl)-5-(5,6-dichloro-1H-benzimidazol-1-yl)-1,2-cyclopentanediyl diacetate as white crystals from ethanol-water (2.6 g, 53%), 1H-NMR(DMSO-d$_6$) consistent with structure.

(±)(1R*,2S*,3R*,5R*)-3-(Acetoxymethyl)-5-(5,6-dichloro-1H-benzimidazol-1-yl)-1,2-cyclopentanediyl diacetate (2.5 g, 5.7 mmol) was dissolved in dry dioxane (15 mL) and the solution refluxed while freshly recrystallized N-bromosuccinimide (2.10 g, 11.5 mmol) was added all at once. After 5 minutes of reflux, the red-brown solution was evaporated in vacuo to a red oil. A chloroform solution of this oil was washed with water and then dried (sodium sulfate). The chloroform solution was concentrated to an oil which was chromatographed on silica gel. Product-containing fractions were eluted with 2–4% methanol-chloroform. Crystallization from ethyl acetate-hexanes gave as off-white solid (1.5 g, 50%); 1H-NMR(DMSO-d$_6$)consistent with structure of title compound. Such a sample was rechromatographed on silica gel with elution by chloroform to give (±)(1R*,2S*,3R*,5R*)-3-(acetoxymethyl)-5-(2-bromo-5,6-dichloro-1H-benzimidazol-1-yl)-1,2-cyclopentanediyl diacetate as white crystals, after crystallization from ethyl acetate-hexanes, m.p. 166°–167° C.; 1H-NMR(DMSO-d$_6$) δ: 8.14 and 7.96 (both s, 1 each, 2 aromatic CH), 5.6–5.35 (m, 3,2 OCH and NCH), 4.4–4.1 (m, 2, OCH$_2$), 2.8–2.4 (m overlapping solvent, 2 CH), 2.4–2.1 (m overlapping s at 2.25, total 4, CH and CH$_3$), 2.04 (s, 3, CH$_3$), 1.37 (s, 1, CH$_3$); mass spectrum(CI): 525(53), 523(100), 521(54, M+1).

Anal. Calcd for C$_{19}$H$_{19}$N$_2$BrCl$_2$O$_6$: C, 43.70; H, 3.67; N, 5.37; total halogen as Cl, 20.37. Found: C, 43.65; H, 3.68; N, 5.35; total halogen as Cl, 20.32.

EXAMPLE 40

(±)(1R*,2S*,3S*,5S*)-3-(Acetoxymethyl)-5-(2-bromo-5,6-dichloro-1H-benzimidazol-1-yl)-1,2-cyclopentanediyl diacetate (±)(1R*,2S*,3S*,5S*)-3-(Acetoxymethyl)-5-(5,6-dichloro-1H-benzimidazol-1-yl)-1,2-cyclopentanediyl diacetate (4.20 g, 9.48 mmol) was refluxed in dry dioxane (25 mL) while freshly recrystallized N-bromosuccinimide (3.37 g, 18.9 mmol) was added all at once. After 5 minutes of reflux, volatiles were removed in vacuo. The residue was partitioned between water and chloroform. The chloroform layer was dried (sodium sulfate), and evaporated to an oil which was chromatographed on silica gel with elution by 1:1 hexanesoethyl acetate. Resolidification from ethanol-water gave title compound as white powder (3.10 g, 63%), m.p. 157°–158.5° C.; 1H-NMR(DMSO-d$_6$) identical to that of the sample described in Example 3.

Anal. Calcd. for C$_{19}$H$_{19}$N$_2$BrCl$_2$O$_6$: C, 43.71; H, 3.67: N, 5.37; total halogen as Cl, 20.37. Found: C, 43.66; H, 3.72; N, 5.34; total halogen as Cl, 20.32.

EXAMPLE 41

(±)-(1R*,2S*,3S*,5S*)-3-(Acetoxymethyl)-5-(2-amino-4,5-dichloroanilino)-1,2-cyclopentanediyl diacetate (±)-(1R*,2S*,3S*,5S*)-3-(Acetoxymethyl)-5-(4,5-dichloro-2-nitroanilino)-1,2-cyclopentanediyl diacetate (4.30 g, 9.28 mmol) in isopropanol (250 mL) was shaken with Raney nickel (Aldrich, slurry in water, 400 mg wet) under hydrogen (50 psi) on a Parr shaker for 2.75 hours. Catalyst was filtered off with Celite and the filtrate-wash (350 mL) stored at −5° C. Yellow crystals of title compound formed slowly (2.35 g, 58%), m.p. 124°–125° C.; 1H-NMR(DMSO-d$_6$) δ: 6.70 and 6.57 (both s, 1 each, 2 aromatic CH), 5.15–4.9 (m, 5, NH$_2$, NH, and 2 OCH), 4.2–4.0 (m, 2, CH$_2$O ), 3.9–3.75 (m, 1, NCH), 2.5–2.4 (m overlapping solvent, CH$_2$), 2.07, 2.04, and 2.01 (all s, 9,3 CH$_3$), 1.4–1.2 (m, 1, CH); mass spectrum(CI): 433(M+1)

Anal. Calcd. for C$_{18}$H$_{22}$N$_2$Cl$_2$O$_6$: C, 49.90; H, 5.12; N, 6.47; Cl, 16.37. Found: C, 50.00; H, 5.13; N, 6.38; Cl, 16.28.

Concentration of the mother liquor gave additional title compound as yellow powder (1.00g, 25 %) with sufficient purity for use (Example 44).

EXAMPLE 42

(±)-(1R*,2S*,3S*,5S*)-5-(5,6-Dichloro-2-methyl-1H-benzimidazol-1-yl)-3-(hydroxymethyl)-1,2-cyclopentanediol (±)-(1R*,2S*,3S*,5S*)-3-(Acetoxymethyl)-5-(4,5-dichloro-2-nitroanilino)-1,2-cyclopentanediyl diacetate (1.00 g, 2.16 mmol), Raney nickel (Aldrich, slurry in water, 100 mg wet), and isopropanol (200 mL) were shaken under hydrogen (50 psi) for 1.25 hours. Catalyst was filtered off with Celite and the filtrate-wash evaporated to dryness. The residual yellow oil was dissolved in triethylorthoaceate (20 mL) with 1 drop of methanesulfonic acid and the solution stirred at ambient temperature for 18 hours. Volatiles were removed in vacuo and the residue stirred in dioxane (20 mL)-1N sodium hydroxide (10 mL) for 5 hours at ambient temperature. The pH was then adjusted to 1 with concentrated hydrochloric acid and stirring continued for 15 minutes, at which point TLC (silica gel, developed with 20 % methanol-chloroform) showed one UV-absorbing spot at $R_f$ 0.25. The solution was neutralized with sodium hydroxide and volatiles evaporated in vacuo. The residue was chromatograped on a silica gel column and title compound eluted with 10–15% methanol-chloroform. Crystallization from ethanol-methanol-water gave (±)-(1R*,2S*,3S*,5S*)-5-(5,6-dichloro-2-methyl-1H-benzimidazol-1-yl)-3-(hydroxymethyl)-1,2-cyclopentanediol as fine white crystals (0.482 g, 67%), m.p. 222°–226° C.; 1H-NMR(DMSO-d$_6$) δ: 8.30 and 7.72 (both s, 2,2 aromatic CH), 5.0–4.8 (m, 3,2 OH and NCH), 4.56 (t, J=5.1 Hz, 1, CH$_2$OH), 4.2–4.1 (m, 2,2 OCH), 3.8–3.5 (m, 2, CH$_2$O ), 2.58 (s, 3, CH$_3$), 2.4–2.2 (m, 1, CH), 2.2–1.9 (m, 2, CH$_2$); mass spectrum (CI): 332 (M+1).

Anal. Calcd. for $C_{14}H_{16}N_2Cl_2O_3$: C, 50.78; H, 4.87; N, 8.46; Cl, 21.24. Found: C, 50.72; H, 4.91; N, 8.54; Cl, 21.13.

EXAMPLE 43

(±)-(1R*,2S*,3S*,5S*)-5-(5,6-Dichloro-2-ethyl-1H-benzimidazol-1-yl)-3-(hydroxymethyl)-1,2-cyclopentanediol In the same manner as Example 42, (±)-(1R*,2S*,3S*,5S*)-3-(acetoxymethyl)-5-(4,5-dichloro-2-nitroanilino)-1,2-cyclopentanediyl diacetate (1.00 g, 2.16 mmol) was converted to title compound using triethylorthopropionate (Aldrich, 97%, 22 mL) for the benzimidazole formation. Solidification from ethanol-water gave (±)-(1R*,2S*,3S*,5S*)-5-(5,6-dichloro-2-ethyl-1H-benzimidazol-1-yl)-3-(hydroxymethyl)-1,2-cyclopentanediol as white powder (0.463 g, 63%), m.p. 191°-193° C.; $^1$H-NMR(DMSO-d$_6$) δ: 8.10 and 7.86 (both s, 2,2 aromatic CH), 5.10 (t, J=4.7 Hz, 1, OH), 4.94 (d, J=6.9 Hz, 1, OH), 4.8-4.6 (m overlapping d at 4.71, J=3.9 Hz, total 2, NCH and OH), 4.5-4.3 (m, 1, OCH), 3.9-3.8 (m, 1, OCH), 3.75-3.45 (m, 2, OCH$_2$), 2.93 (q, J=7.4 Hz, 2, CH$_2$CH$_3$), 2.2-2.0 (m, 3, CH$_2$ and CH), 1.34 (t, J=7.4 Hz, 3, CH$_3$); mass spectrum (CI): 345 (M+1).

Anal. Calcd. for $C_{15}H_{18}N_2Cl_2O_3 \cdot 0.25\ H_2O$: C, 51.52; H, 5.33; N, 8.01; Cl, 20.27. Found: C, 51.59; H, 5.31; N, 8.05; Cl, 20.19.

EXAMPLE 44

(±)-(1R*,2S*,3S*,5S*)-3-(Acetoxymethyl)-5-(5,6-dichloro-2,3-dihydro-2-thioxo-1H-benzimidazol-1-yl)-1,2-cyclopentanediyl diacetate (±)-(1R*,2S*,3S*,5S*)-3-(Acetoxymethyl)-5-(2-amino-4,5-dichloroanilino)-1,2-cyclopentanediyl diacetate (2.25 g, 5.19 mmol), 1,1'-thiocarbonyldiimidazole (Aldrich, 1.03 g, 5.19 mmol as 90%), and toluene (125 mL) were refluxed for 30 minutes. Additional 1,1'-thiocarbonyldiimidazole (0.51 g) was added and reflux continued for an additional 15 minutes. Volatiles were evaporated in vacuo and the residual yellow oil dissolved in chloroform (75 mL) and washed with water (2×25 mL). The chloroform layer was dried (sodium sulfate) and concentrated in vacuo to a yellow oil. Crystallization from ethyl acetate-hexanes gave tan crystals (2.30 g, 93%) with $^1$NMR identical to that described below. Such a sample was further purified by elution from a silica gel column with 4% methanol-chloroform before crystallization from ethyl acetate-hexanes to give (±)-(1R*,2S*,3S*,5S*)-3-(acetoxymethyl)-5-(5,6-dichloro-2,3-dihydro-2-thioxo-1H-benzimidazol-1-yl)-1,2-cyclopentanediyl diacetate as off-white crystals, m.p. 208°-209° C.; $^1$H-NMR(DMSO-d$_6$) δ: 13.2 (br s, 1, NH), 8.05 and 7.39 (both s, 2,2 aromatic CH), 6.0-5.8 (m, 1, OCH), 5.6-5.3 (m, 2, OCH and NCH), 4.40-4.15 (m, 2, OCH$_2$), 2.6-2.5 (m overlapping solvent, CH), 2.4-2.0 (m overlapping two s at 2.09 and 2.06, total 8, CH$_2$ and 2 CH$_3$), 1.93 (s, 3, CH$_3$); mass spectrum(CI): 475 (M+1).

Anal. Calcd. for $C_{19}H_{20}N_2Cl_2O_6S$: C, 48.01; H, 4.24; N, 5.89; Cl, 14.92; S, 6.75. Found: C, 48.11; H, 4.22; N, 5.90; Cl, 14.85; S, 6.74.

EXAMPLE 45

(±)-(1R*,2S*,3S*,5S*)-5-[2-(Benzylthio)-5,6-dichloro-1H-benzimidazol-1-yl]-3-(hydroxymethyl)-1,2-cyclopentanediol A mixture of (±)-(1R*,2S*,3S*,5S*)-3-(acetoxymethyl)-5-(5,6-dichloro-2,3-dihydro-2-thioxo-1H-benzimidazol-1-yl)-1,2-cyclopentanediyl diacetate (0.50 g, 1.05 mmol), benzyl bromide (0.3 mL, 2.5 mmol) and anhydrous potassium carbonate (0.145 g, 1.05 mequiv as 98%) in dioxane (5 mL) was stirred vigorously at ambient temperature for 2.5 days. Volatiles were evaporated in vacuo and the residue partitioned between chloroform and water. The chloroform layer was dried(sodium sulfate) and concentrated to an oil which was stirred in ammonia-methanol (40 mL of half-saturated) for 18 hours. Volatiles were evaporated and the residue solidified from 3:1 methanol-water to give title compound as a white powder (300 mg, 65%), m.p. 160°-162° C.; $^1$H-NMR(DMSO-d$_6$) δ: 8.04 and 7.89 (both s, 1 each, 2 aromatic CH), 7.5-7.2 (m, 5, C$_6$H$_5$), 5.06 (t, J=4.7 Hz, 1, OH), 4.98 (d, J=6.2 Hz, 1, OH), 4.75-4.55 (m overlapping d at 4.68, J=3.7 Hz, and s at 4.63, total 4, NCH, OH, and SCH$_2$); mass spectrum(CI): 439 (M+1).

Anal. Calcd. for $C_{20}H_{20}N_2Cl_2O_3S$: C, 54.68; H, 4.59; N, 6.38; total halogen as Cl, 16.14; S,7.30. Found: C, 54.75; H, 4.62; N, 6.38; total halogen as Cl, 16.21; S,7.27.

EXAMPLE 46

(±)-(1R*,2S*,3S*,5S*)-5-(5,6-Dichloro-2-methoxy-1H-benzimidazol-1-yl)-3-(hydroxymethyl)-1,2-cyclopentanediol Sodium (spheres, 0.10 g, 4.8 mequiv) were added to dry methanol (15 mL). (±)-(1R*,2S*,3S*,5S*)-3-(Acetoxymethyl)-5-(2-bromo-5,6-dichloro-1H-benzimidazol-1-yl)-1,2-cyclopentanediyl diacetate (0.560 g, 0.958 mmol) was added to the sodium methoxide in methanol and the solution stirred at ambient temperature under nitrogen for 5 hours. The solution was then neutralized with 1N hydrochloric acid and volatiles removed in vacuo. The residual solid was chromatographed on silica gel. (±)-(1R*,2S*,3S*,5S*)-5-(5,6-Dichloro-2-methoxy-1H-benzimidazol-1-yl)-3-(hydroxymethyl)-1,2-cyclopentanediol was eluted with 10% methanol-chloroform as a white powder, after trituration with diethyl ether (0.211 g, 64%), m.p. 204°-206° C. dec; $^1$H-NMR(DMSO-d$_6$) δ: 7.82 and 7.67 (both s, 2, aromatic CH), 4.9 (m, 2,2 OH), 4.7-4.6 (m overlapping d at 4.61, J=4.1 Hz, 2 total, NCH and OH), 4.4-4.3 (m, 1, OCH), 4.11 (s, 3, OCH$_3$), 3.8 (m, 1, OCH), 3.6-3.4 (m, 2, OCH$_2$), 2.1-2.0 (m, 2, CH$_2$), 1.9-1.8 (m, 1, CH); mass spectrum (CI): 347(M+1).

Anal. Calcd. for $C_{14}H_{16}N_2Cl_2O_4$: C, 48.43; H, 4.65:N, 8.07; Cl, 20.42. Found: 48.23; H, 4.71; N, 7.98; Cl, 20.51.

EXAMPLE 47

(±)-(1R*,2S*,3S*,5S*)-5-(5,6-Dichloro-2-phenoxy-1H-benzimidazol-1-yl)-3-(hydroxymethyl)-1,2-cyclopentanediol Phenol (72 mg, 0.77 mmol) and anhydrous potassium carbonate (106 mg, 0.77 mmol) were stirred in dry N,N-dimethylformamide (5 mL) under nitrogen for 1.0 hour. (±)(1R*,2S*,3S*,5S*)-3-(Acetoxymethyl)-5-(2-bromo-5,6-dichloro-1H-benzimidazol-1-yl)-1,2-cyclopentanediyl diacetate (400 mg, 0.770 mmol) was added and the mixture stirred at 80° C. (oil bath) for 18 hours. Volatiles were removed in vacuo and the residue partitioned between chloroform and water. The chloroform layer was dried (sodium sulfate) and volatiles evaporated. The residual oil was stirred in 4N ammonia in methanol (30 mL) at ambient temperature for 18 hours. Evaporation and chromatography of the residue on silica gel with elution by 2% methanol-chloroform gave (±)-(1R*,2S*,3S*,5S*)-5-(5,6-dichloro-2-phenoxy-1H-benzimidazol-1-yl)-3-(hydroxymethyl)-1,2-cyclopentanediol as white solid foam from ethyl acetate (215 mg, 68%); $^1$H-NMR(DMSO-d$_6$) δ: 7.98 and 7.71 (both s, 2, aromatic CH), 7.6–7.3 (m, 5, C$_6$H$_5$), 5.07 (d, J=6.4 Hz, 1, OH), 5.0–4.75 (m overlapping t at 4.95, J=3.1 Hz, total 2, NCH and OH), 4.71 (d, J=3.9 Hz, 1, OH), 4.5–4.35 (m, 1, OCH), 3.9–3.8 (m, 1, OCH), 3.7–3.4 (m, 2, OCH$_2$), 2.3–1.9 (m, 3, CH$_2$ and CH); mass spectrum (CI): 409 (M+1).

Anal. Calcd. for C$_{19}$H$_{18}$N$_2$Cl$_2$O$_4$: C, 55.15; H, 4.51:N, 6.77; Cl, 17.14. Found: C, 55.14; H, 4.52; N, 6.72; Cl, 17.07.

EXAMPLE 48

(±)-(1R*,2S*,3S*,5S*)-5-[5,6-Dichloro-2-(cyclopropylamino)-1H-benzimidazol-1-yl]-3-(hydroxymethyl)-1,2-cyclopentanediol (±)(1R*,2S*,3S*,5S*)-3-(Acetoxymethyl)-5-(2-bromo-5,6-dichloro-1H-benzimidazol-1-yl)-1,2-cyclopentanediyl diacetate (500 mg, 0.958 mmol) was dissolved in absolute ethanol (5 mL) and cyclopropylamine (0.66 mL, 9.6 mmol) was added. The solution was refluxed under nitrogen for two hours. Additional cyclopropylamine (0.66 mL) was added and reflux continued for an additional 18 hours. The solution was cooled and methanol saturated with ammonia at 0° C. (5 mL) was added. After two days at ambient temperature, volatiles were removed in vacuo and the residue chromatographed on silica gel. (±)-(1R*,2S*,3S*,5S*)-5-[5,6-Dichloro-2-(cyclopropylamino)-1H-benzimidazol-1-yl]-3-(hydroxymethyl)-1,2-cyclopentanediol was eluted with 7% methanol-chloroform and solidified from ethyl acetate-hexanes to white powder (210 mg, 59%), m.p. 223°–224° C.; $^1$H-NMR(DMSO-d$_6$) δ: 7.64 and 7.46 (both s, 2, aromatic CH), 7.11 (m, 1, NH), 5.11 (t, J=4.3 Hz, 1, OH), 4.77 (d, J=7.0 Hz, 1, OH), 4.67 (d, J=3.7 Hz, 1, OH), 4.65–4.30 (m, 2, OCH and NCH), 3.85–3.75 (m, 1, OCH), 3.7–3.4 (m, 2, OCH$_2$), 2.85–2.70 (m, 1, NCH of cyclopropyl), 2.15–1.80 (m, 3, CH$_2$ and CH of cyclopentane), 0.80–0.50 (m, 4,2 CH$_2$ of cyclopropyl); mass spectrum (CI): 372(M+1).

Anal. Calcd. for C$_{16}$H$_{19}$N$_3$Cl$_2$O$_3$: C, 51.63; H, 5.15:N, 11.29; Cl, 19.05. Found: C, 51.41; H, 5.20; N, 11.19; Cl, 19.16.

EXAMPLE 49

(±)-(1R*,2S*,3S*,5S*)-5-[5,6-Dichloro-2-(dimethylamino)-1H-benzimidazol-1-yl]-3-(hydroxymethyl)-1,2-cyclopentanediol (±)(1R*,2S*,3S*,5S*)-3-(Acetoxymethyl)-5-(2-bromo-5,6-dichloro-1H-benzimidazol-1yl)-1,2-cyclopentanediyl diacetate (500 mg, 0.958 mmol) and 40% aqueous N,N,-dimethylamine (6.0 mL) were refluxed for 2.5 hours. Volatiles were removed in vacuo and the residue was solidified from 1:1 ethanol-water to give (±)-(1R*,2S*,3S*,5S*)-5-[5,6-dichloro-2-(dimethylamino)-1H-benzimidazol-1-yl]-3-(hydroxymethyl)-1,2-cyclopentanediol as white powder (263 mg, 76%), m.p. 190°–193° C.; $^1$H-NMR(DMSO-d$_6$) δ: 7.89 and 7.66 (both s, 2, aromatic CH), 5.07 (t, J=4.5 Hz, 1, OH), 4.97 (d, J=5.9 Hz, 1, OH), 4.8–4.6 (m overlapping d at 4.62, J=3.5 Hz, total 2, NCH and OH), 4.55–4.4 (m, 1, OCH), 3.9–3.75 (m, 1, OCH), 3.7–3.4 (m, 2, OCH$_2$), 2.92 (s, 6,2 CH$_3$), 2.2–1.9 (m, 3, CH$_2$ and CH); mass spectrum (CI): 360(M+1).

Anal. Calcd. for C$_{15}$H$_{19}$N$_3$Cl$_2$O$_3$.0.65 H$_2$: C, 48.44; H, 5.50:N, 11.30; Cl, 19.06. Found: C, 48.39; H, 5.31; N, 10.88; Cl, 19.49.

EXAMPLE 50

(±)-(1R*,2S*,3S*,5S*)-5-[5,6-Dichloro-2-(cyclopentylamino)-1H-benzimidazol-1-yl]-3-(hydroxymethyl)-1,2-cyclopentanediol (±)(1R*,2S*,3S*,5S*)-3-(Acetoxymethyl)-5-(2-bromo-5,6-dichloro-1H-benzimidazol-1-yl)-1,2-cyclopentanediyl diacetate (500 mg, 0.958 mmol) and cyclopentylamine (0.95 mL, 9.6 mmol) were refluxed in absolute ethanol (5 mL) for 3.5 hours. Methanolic ammonia (25 mL saturated at 0° C) was added and stirring continued for an additional 18 hours. Volatiles were removed in vacuo and the residue chromatographed on silica gel. Elution with 6–8% methanol-chloroform followed by crystallization from ethyl acetate-hexanes gave (±)-(1R*,2S*,3S*,5S*)-5-[5,6-dichloro-2-(cyclopentylamino)-1H-benzimidazol-1-yl]-3-(hydroxymethyl)-1,2-cyclopentanediol as white powder (155 mg, 41%), m.p. 270°–271° C. dec; $^1$H-NMR(DMSO-d$_6$)δ: 7.58 and 7.37 (both s, 2,2 aromatic CH), 6.67 (d, J=6.8 Hz, 1, NH), 5.11 (t, J=4.5 Hz, 1, OH), 4.79 (d, J=7.4 Hz, 1, OH), 4.68 (d, J=3.7 Hz, 1, OH), 4.6–4.5 (m, 1, NCH), 4.4–4.3 (m, 1, OCH), 4.2–4.1 (m, 1, NCH of cyclopentylamino), 3.79–3.77 (m, 1, OCH), 3.75–3.5 (m, 2, OCH$_2$), 2.1–1.8 (m, 5,2CH$_2$ and CH), 1.7–1.3 (m, 6,3 CH$_2$); mass spectrum(CI): 400(M+1 ).

Anal. Calcd. for C$_{18}$H$_{23}$N$_3$Cl$_2$O$_3$.0.10 EtOAc: C, 54.02; H, 5.86:N, 10.27; Cl, 17.33. Found: C, 53.77; H, 5.83; N, 10.30; Cl, 17.52.

EXAMPLE 51

(±)(1R*,2S*,3S*,5S*)-3-(Acetoxymethyl)-5-(5,6-dichloro-2-iodo-1H-benzimidazol-1-yl)-1,2-cyclopentanediyl diacetate (±)(1R*,2S*,3S*,5S*)-3-(Acetoxymethyl)-5-(5,6-dichloro-1H-benzimidazol-1-yl)-1,2-cyclopentanediyl diacetate (500 mg, 1.13 mmol) was dissolved in dry N,N-dimethylformamide (4 mL) and heated to 95°–105° C. N-Iodosuccinimide (534 mg, 2.3 mmol as 95%) was added in portions over 5.5 hours. Volatiles were removed in vacuo and the residue chromatographed on silica gel. Elution with 10% ethyl acetate-hexanes followed by solidification from ethanol-water gave (±)(1R*,2S*,3S*,5S*)-3-(acetoxymethyl)-5-(5,6-dichloro-2-iodo-1H-benzimidazol-1-yl)-1,2-cyclopentanediyl diacetate as a white powder (255 mg, 40%), m.p.152.5°–153° C.; $^1$H-NMR(DMSO-d$_6$) δ: 8.32 and 7.94 (both s, 2,2 aromatic CH), 5.8–5.7 (m, 1, OCH), 5.4–5.3(m, 1, OCH), 5.2–5.0 (m, 1, NCH), 4.35–4.2 (m, 2, OCH$_2$), 2.7–2.6 (m, 1, CH), 2.35–2.25 (m, 2, CH$_2$), 2.11, 2.08, and 1.93 (all s, 3 each, 3 CH$_3$); mass spectrum(CI) 569 (M+1).

Anal. Calcd. for C$_{19}$H$_{19}$N$_2$Cl$_2$IO$_6$: C, 40.10; H, 3.37; N, 4.92; total halogen as Cl, 18.69. Found: C, 40.27; H, 3.39; N, 4.88; total halogen as Cl, 18.63.

EXAMPLE 52

(±)-(1R*,2S*,3S*,5S*)-5-(5,6-Dichloro-2-iodo-1H-benzimidazol-1-yl)-3-(hydroxymethyl)-1,2-cyclopentanediol Sodium carbonate (40 mg, 0.37 mmol) was dissolved in water (0.7 mL) and methanol (3 mL) and ethanol (3 mL) were added. To this stirred mixture was added (±)(1R*,2S*,3S*,5S*)-3-(acetoxymethyl)-5-(5,6-dichloro-2-iodo-1H-benzimidazol-1-yl)-1,2-cyclopentanediyl diacetate (215 mg, 0.37 mmol). After 2 hours at ambient temperature, acetic acid was added to adjust the pH to 7 and volatiles were evaporated in vacuo. Resolidification of the residual solid from 3:1 ethanol-water gave (±)-(1R*,2S*,3S*,5S*)-5-(5,6-dichloro-2-iodo-1H-benzimidazol-1-yl)-3-(hydroxymethyl)-1,2-cyclopentanediol as a white powder (153 mg, 94%), m.p. 209°–210° C. dec.; $^1$H-NMR(DMSO-d$_6$) δ: 8.22 and 7.91 (both s, 2,2 aromatic CH), 5.12 (t, J=4.5 Hz, 1, OH), 4.95 (d, J=6.2 Hz, 1, OH), 4.9–4.8 (m, 1, NCH), 4.70 (t, J=3.5 Hz, 1, OH), 4.6–4.5 (m, 1, OCH), 3.9–3.8 (m, 1, OCH), 3.7–3.6 and 3.55–3.45 (both m, 1 each, OCH$_2$), 2.2–2.0 (m, 3, CH$_2$ and CH); mass spectrum(CI): 443 (M+1).

Anal. Calcd. for C$_{13}$H$_{13}$N$_2$Cl$_2$IO$_2$: C, 35.24; H, 2.96; N, 6.32; total halogen as Cl, 24.01. Found: C, 35.30; H, 3.01; N, 6.23; total halogen as Cl, 23.95.

EXAMPLE 53

(1S,4R)-[4-(4,5-Dichloro-2-nitroanilino)-2-cyclopenten-1-yl]methanol (−)-(1R,4S)-tert-Butyl N-[4-hydroxymethyl)-2-cyclopentenol-1-yl]carbamate (15.00 g, 70.3 mmol) was converted by the method of Example 33 to (1S,4R)-[4-(4,5-dichloro-2-nitroanilino)-2-cyclopenten-1-yl]methanol, isolated as a yellow powder after elution from a silica gel column with 1:1 hexanes-chloroform and resolidification from ethyl acetate-hexanes (9.97 g, 47%), m.p. 94.5°–96.5° C.; $^1$H-NMR(DMSO-d$_6$) δ: 8.24 (s, 1, benzimidazole CH), 8.09 (d, J=8.1 Hz, 1, NH), 7.51 (s, 1, benzimidazole CH), 5.95 and 5.85 (both m, 2, CH=CH), 4.9–4.7 (m overlapping t at 4.78, J=5.1 Hz, total 2, CHN and OH), 3.4 (m, 2, CH$_2$O), 2.80 (m, 1, CH), 2.6–2.4 (m overlapping solvent, CH), 1.5–1.4 (m, 1, CH); mass spectrum(CI): 303 (M+1); [α]$^{20}_{589}$+199°, [α]$^{20}_{578}$+222°, [α]$^{20}_{546}$+333° (c=0.267, methanol).

Anal. Calcd. for C$_{12}$H$_{12}$N$_2$Cl$_2$O$_3$.0.18 C$_6$H$_{14}$: C, 49.30; H, 4.59; N, 8.79; Cl, 22.25. Found: C, 49.64; H, 4.64; N, 8.68; Cl, 22.10.

EXAMPLE 54

(1S,2R,3R,5R)-5-(4,5-Dichloro-2-nitroanilino)-3-(hydroxymethyl)-1,2-cyclopentanediol and (1R,2S,3R,5R)-5-(4,5-dichloro-2-nitroanilino)-3-(hydroxymethyl)-1,2-cyclopentanediol To a solution of (1S,4R)-[4-(4,5-dichloro-2-nitroanilino)-2-cyclopenten-1-yl]methanol (8.60 g, 27.6 mmol) and N-methylmorpholine N-oxide (Aldrich, 60% aqueous solution, 5.02 mL, 29.0 mmol) in acetone (90 mL) was added osmium tetroxide (Aldrich, 2.5% in t-butyl alcohol, 0.51 mL). After stirring at ambient temperature for 18 hours, an additional 0.25 mL of 60% aqueous N-methylmorpholine N-oxide was added and the solution stirred for an additional 5 hours. Volatiles were evaporated in vacuo and the residue recrystallized twice from 95% ethanol to give (1S,2R,3R,5R)-5-(4,5-dichloro-2-nitroanilino)-3-(hydroxymethyl)-1,2-cyclopentanediol as yellow powder (1.78 g, 19%), m.p. 197°–199° C.; $^1$H-NMR(DMSO-d$_6$) δ: 8.23 (s, 1, benzimidazole CH), 8.1 (d, J=7.0 Hz, 1, NH), 7.50 (s, 1, benzimidazole CH), 5.02 (d, J=4.9 Hz, 1, OH), 4.74 (t, J=5.1 Hz, 1, CH$_2$OH), 4.58 (d, J=5.1 Hz, 1, OH), 4.0–3.8 (m, 1, NCH), 3.8–3.7 (m, 2,2 OCH), 3.5–3.4 (m, 2, CH$_2$O), 2.45–2.25 (m, 1, CH), 2.1–1.9 (m, 1, CH), 1.4–1.2 (m, 1, CH); mass spectrum(CI): 337 (M+1); [α]$^{20}_{589}$−106°, [α]$^{20}_{578}$−118°, [α]$^{20}_{546}$−182° (c=0.273, methanol).

Anal. Calcd. for C$_{12}$H$_{14}$N$_2$Cl$_2$O$_5$: C, 42.75; H, 4.19; N, 8.31; Cl, 21.03. Found: C, 42.84; H, 4.21; N, 8.24; Cl, 21.09.

Chromatography of the mother liquor contents on silica gel gave the (1R,2S)-isomer on elution with 7–8% methanol-chloroform; two resolidifications from 90% ethanol gave (1R,2S,3R,5R)-5-(4,5-dichloro-2-nitroanilino)-3-(hydroxymethyl)-1,2-cyclopentanediol as a yellow powder (1.57 g, 17%), m.p. 179° 181° C.; $^1$H-NMR(DMSO-d$_6$) δ: 8.70 (d, J=7.1 Hz, 1, NH), 8.22 and 7.32 (both s, 1 each, 2 benzimidazole CH), 5.28 (d, J=5.6 Hz, 1, OH), 4.77 (d, J=3.9 Hz, 1 OH), 4.45 (t, J=4.9 Hz, 1, CH$_2$OH), 4.1–3.9 (m, 3,2 OCH and NCH), 3.6–3.5 and 3.45–3.35 (both m partially overlapping H$_2$O, 2, CH$_2$O), 2.45–2.25 (m, 1, CH), 2.1–3.9 (m, 1, CH), 1.35–1.25 (m,1, CH); mass spectrum(CI): 337(M+1); [α]$^{20}_{589}$−15.6°, [α]$^{578}$−13,2°, [α]$^{20}_{546}$−4.00° (c=0.250, methanol).

Anal. Calcd. for C$_{12}$H$_{14}$N$_2$Cl$_2$O$_5$: C, 42.75; H, 4.19; N, 8.31; Cl, 21.03. Found: C, 42.87; H, 4.15; N, 8.30; Cl, 21.14.

Elution with 8–10% methanol-chloroform gave white solid (2.9 g) which $^1$H-NMR showed to be an approximately 1:1 mixture of the two isomers.

Continued elution of the column with 10–20% methanol-chloroform gave fractions containing additional (1S,2R,3R,5R)-5-(4,5-dichloro-2-nitroanilino)-3-(hydroxymethyl)-1,2-cyclopentanediol which solidified from 90% ethanol to white powder (2.23 g) bringing the total yield of this isomer to 43%.

EXAMPLE 55

(1S,2R,3R,5R)-3-(Acetoxymethyl)-5-(4,5-dichloro-2-nitroanilino)-1,2-cyclopentanediyl diacetate (1S,4R)-[4-(4,5-Dichloro-2-nitroanilino)-2-cyclopenten-1-yl]methanol (3.75 g, 11.1 mmol) was acetylated in pyridine-acetic anhydride as in Example 38. The crude product was eluted from a silica gel column with 2% methanol-chloroform and solidified from ethyl acetate to give (1S,2R,3R,5R)-3-(acetoxymethyl)-5-(4,5-dichloro-2-nitroanilino)-1,2-cyclopentanediyl diacetate as yellow powder (5.13 g, 100%), NMR identical to that of Example 1. Such a sample was crystallized from ethyl acetate-hexanes to give title compound as yellow powder, m.p. 128°–130° C.; $^1$H-NMR(DMSO-d$_6$) and mass spectrum (CI) identical to those of Example 1.; [α]$^{20}_{589}$−95.8°, [α]$^{20}_{578}$−107°, [α]$^{20}_{546}$−165° (c=0.259, methanol).

Anal. Calcd. for C$_{18}$H$_{20}$N$_2$Cl$_2$O$_8$: C, 46.67; H, 4.35; N, 6.05; Cl, 15.31. Found: C, 46.74; H, 4.36; N, 5.96; Cl, 15.38.

EXAMPLE 56

(1S,2R,3R,5R)-3-(Acetoxymethyl)-5-(5,6-dichloro-1H-benzimidazol-1-yl)-1,2-cyclopentanediyl diacetate (1S,2R,3R,5R)-3-(Acetoxymethyl)-5-(4,5-dichloro-2-nitroanilino)-1,2-cyclopentanediyl diacetate (4.42 g, 9.97 mmol) was converted to title compound as with the racemic sample described in Example 2. Crude product was chromatographed on silica gel with elution by 5% methanol-chloroform and solvents evaporated to give (1S,2R,3R,5R)-3-(acetoxymethyl)-5-(5,6-dichloro-1H-benzimidazol-1-yl)-1,2-cyclopentanediyl diacetate as an off-white solid foam from ethanol (4.0 g, 90%); $^1$H-NMR(DMSO-d$_6$) and mass spectrum(CI) identical to those of racemate described in Example 2; $[\alpha]^{20}_{589}+25.20$, $[\alpha]^{20}_{578}+26.7°$, $[\alpha]^{20}_{546}+30.6°$ (c=0.255, methanol).

Anal. Calcd. for $C_{19}H_{20}N_2Cl_2O_6$: C, 51.49; H, 4.55; N, 6.32; Cl, 16.00. Found: C, 51.33; H, 4.58; N, 16.27; Cl, 15.90.

EXAMPLE 57

(1S,2R,3R,5R)-5-(5,6-Dichloro-1H-benzimidazol-1-yl)-3-(hydroxymethyl)-1,2-cyclopentanediol (1S,2R,3R,5R)-3-(Acetoxymethyl)-5-(5,6-dichloro-1H-benzimidazol-1-yl)-1,2-cyclopentanediyl diacetate (0.96 g, 2.17 mmol) and sodium carbonate (0.230 g, 2.17 mmol) were stirred in water (3 mL)-ethanol(15 mL)-methanol(15 mL) at ambient temperature for 24 hours. The pH was adjusted to 7 with acetic acid and the volatiles removed in vacuo. The residual solid was slurried in water (25 mL) and filtered. Resolidification from 2:1 ethanol-methanol gave (1 S,2R,3R,5R)-5-(5,6-dichloro-1H-benzimidazol-1-yl)-3-(hydroxymethyl)-1,2-cyclopentanediol as white powder (408 mg, 60%), m.p. 222°-225° C.; $^1$H-NMR(DMSO-d$_6$) δ: 8.49, 8.09, and 7.96 (all s, 1 each, 3 benzimidazole CH), 5.04 (d, J=7.0 Hz, 1, OH), 4.87 (t, J=5.1 Hz, 1, CH$_2$OH), 4.84.6 (m overlapping d at 4.76, J=4.3 Hz, 2, NCH and OH), 4.25-4.10 (m, 1, OCH), 3.9-3.8 (m, 1, OCH), 3.6-3.45 (m, 2, CH$_2$O), 2.45-2.25 (m, 1, CH), 2.2-2.0 (m, 1, CH), 1.85-1.65 (m, 1, CH); mass spectrum(CI): 317 (M+1); $[\alpha]^{20}_{578}-12.9°$, $[\alpha]^{20}_{546}-14.1°$ (c=0.255, methanol).

Anal. Calcd. for $C_{13}H_{14}N_2Cl_2O_3$: C, 49.23; H, 4.45; N, 8.83; Cl, 22.36. Found: C, 49.25; H, 4.47; N, 8.83; Cl, 22.46.

EXAMPLE 58

(1S,2R,3R,5R)-5-(2-Bromo-5,6-dichloro-1H-benzimidazol-1-yl)-3-(hydroxymethyl)-1,2-cyclopentanediol (1S,2R,3R,5R)-3-(Acetoxymethyl)-5-(5,6-dichloro-1H-benzimidazol-1-yl)-1,2-cyclopentanediyl diacetate (2.00 g, 4.51 mmol) was dissolved in dry N,N-dimethylformamide (9 mL) and heated to 90° C. N-bromosuccinimide (1.62 g, 9.02 mmol) was added in four portions over 5 hours. Volatiles were evaporated in vacuo. The residue was chromatographed on silica gel and product was eluted with 30-50% ethyl acetate-hexanes as a yellow glass (1.00 g, 43%); $^1$H-NMR(DMSO-d$_6$) consistent with structure. This sample was deblocked with sodium carbonate (203 mg, 1.9 mmol) in water (3 mL)-ethanol(15 mL)-methanol(15 mL) at ambient temperature for 5 hours. The pH was adjusted to 7 with acetic acid. The solution was evaporated to dryness in vacuo and the residue was triturated with water to give white powder which was chromatographed. Elution of a silica gel column with 10-12% methanol-chloroform gave (1S,2R,3R,5R)-5-(2-bromo-5,6-dichloro-1H-benzimidazol-1-yl)-3-(hydroxymethyl)-1,2-cyclopentanediol as white powder after solidification from 1:1 ethanol-methanol (410 mg, 54%), m.p. 212°-215° C.; $^1$H-NMR(DMSO-d$_6$) and mass spectrum identical with those of racemate described in Example 4; $[\alpha]^{20}_{589}-31.2°$, $[\alpha]^{20}_{578}-32.3°$, $[\alpha]^{20}_{546}-37.3°$ (c=0.260, methanol).

Anal. Calcd. for $C_{13}H_{13}N_2BrCl_2O_3$: C, 39.43; H, 3.31; N, 7.07; total halogen as Cl, 26.86. Found: C, 39.62; H, 3.37; N, 7.02; total halogen as Cl, 26.75.

EXAMPLE 59

(1S,2R,3R,5R)-5-(5,6-Dichloro-2-methyl-1H-benzimidazol-1-yl)-3-(hydroxymethyl)-1,2-cyclopentanediol Title compound of Example 55 (514 mg, 1.11 mmol) was reduced with Raney nickel and hydrogen as in Example 56. Catalyst was filtered off, ethanol was evaporated in vacuo, and glacial acetic acid (5 mL) substituted for formic acid. The acetic acid solution was refluxed for several hours. Acetic anhydride (5 mL) was added and reflux continued for 0.5 hour. Volatiles were evaporated in vacuo and the residual dark oil was chromatographed on silica gel. Elution with 4% methanol-chloroform gave fractions containing the triacetate of title compound as a yellow oil (0.46 g) with $^1$NMR consistent with structure. Deacetylation was carried out with sodium carbonate as in Example 57. The solid obtained upon trituration with water was recrystallized from 1:1 methanol ethanol with a few drops of water to give (1S,2R,3R,5R)-5-(5,6-dichloro-2-methyl-1H-benzimidazol-1-yl)-3-(hydroxymethyl)-1,2-cyclopentanediol as white powder (220 mg, 75%), m.p. 222°-224° C.; $^1$H-NMR(DMSO-d$_6$) δ: 8.09 and 7.82 (both s, 1 each, 2 benzimidazole CH), 5.09 (t, J=4.5 Hz, 1, CH$_2$OH), 4.95 (d, J=7.2 Hz, 1, OH), 4.8-4.6 (m overlapping d at 4.75, J=3.9 Hz, 2, NCH and OH), 4.5-4.3 (m, 1, OCH), 3.9-3.8 (m, 1, OCH), 3.7-3.45 (m, 2, CH$_2$O), 2.59 (s overlapping solvent, CH$_3$), 2.3-1.9 (m, 3, CH$_2$ and CH);mass spectrum(CI): 331(M+1); $[\alpha]^{20}_{589}-58.6°$, $[\alpha]^{20}_{578}-62.0°$, $[\alpha]^{20}_{546}-70.8°$ (c=0.250 methanol).

Anal. Calcd. for $C_{14}H_{16}N_2Cl_2O_3$: C, 50.78; H, 4.87; N, 8.46; Cl, 21.41. Found: C, 50.85; H, 4.88; N, 8.45; Cl, 21.32.

EXAMPLE 60

(1R,2S,3R,4R)-5,6-Dichloro-1-[2,3-dihydroxy-4-(hydroxymethyl)cyclopentyl]-1H-benzimidazol-2(3H)-one Title compound of Example 55 (500mg, 1.08 mmol) was reduced with Raney nickel and hydrogen as in Example 56. Catalyst was filtered off, ethanol evaporated in vacuo, and the residual oil dissolved in chloroform (50 mL) and brought to reflux. 1,1'-Carbonyldiimidazole (845 mg, 4.40 mmol) was added in portions while the solution was refluxed for 3.5 hours. The solution was cooled and then extracted with water (2×20 mL), dried (sodium sulfate), and concentrated to a dark oil which was chromatographed on silica gel. Elution with 5% methanol-chloroform gave the triacetate of title compound as a white powder (400 mg, 81%), $^1$H-NMR consistent with structure. Deblocking was carried out in dioxane (10 mL) with sufficient 1N sodium hydroxide to bring the pH to 14. After one hour at ambient temperature, the pH was adjusted to 7 with 1N hydrochloric acid. Volatiles were evaporated in vacuo and the residual solid was chromatographed on silica gel. Product eluted with 10-15% methanol-chloroform and was recrystallized from ethanol-water and then from methanol-water to give (1R,2S,3R,4R)-5,6-dichloro-1-[2,3-dihydroxy-4-(hydroxymethyl)cyclopentyl]-1H-benzimidazol-2(3H)-one as white needles (130 mg, 45%), m.p. 219°–220° C.; $^1$H-NMR(DMSO-d$_6$) δ: 11.2 (br m, 1, imidazole NH), 7.56 and 7.19 (both s, 1 each, 2 benzimidazole CH), 4.9–4.7 (m, 2,2OH), 4.7–4.45 (m, 2, OH and OCH), 4.45–4.3 (m, 1, NCH), 3.80 (m, 1, OCH), 3.50 (m, 2, OCH$_2$), 2.1–1.8 (m, 3, CH$_2$ and CH); mass spectrum(CI): 333(M+1); $[\alpha]^{20}_{589}$−3.60°, $[\alpha]^{20}_{578}$−1.20°, $[\alpha]^{20}_{365}$+32.8° (c=0.253, methanol).

Anal. Calcd. for C$_{13}$H$_{14}$N$_2$Cl$_2$O$_4$: C, 46.87; H, 4.24; N, 8.41; Cl, 21.28. Found: C, 46.98; H, 4.26; N, 8.37; Cl, 21.30.

EXAMPLE 61

(1R,2S,3R,5R)-3-(Acetoxymethyl)-5-(4,5-dichloro-2-nitroanilino)-1,2-cyclopentanediyl diacetate (1R,2S,3R,5R)-5-(4,5-Dichloro-2-nitroanilino)-3-(hydroxymethyl)-1,2-cyclopentanediol (1.30 g, 3.86 mmol) was stirred in pyridine (10 mL)-acetic anhydride (2.2 mL) at ambient temperature for 2 days. Volatiles were evaporated in vacuo and the residue partitioned between chloroform and saturated aqueous sodium bicarbonate. The chloroform layer was dried (sodium sulfate) and concentrated to an oil which was chromatographed on silica gel. Elution with 2% methanol-chloroform gave (1R,2S,3R,5R)-3-(acetoxymethyl)-5-(4,5-dichloro-2-nitroanilino)-1,2-cyclopentanediyl diacetate as yellow needles (1.60 g, 89%), after crystallization from ethyl acetate-hexanes, m.p. 125°–130° C.; $^1$H-NMR(DMSO-d$_6$) and mass spectrum (CI) consistent with structure; $[\alpha]^{20}_{589}$−130.5°, $[\alpha]^{20}_{578}$−140°, $[\alpha]^{20}_{546}$−178° (c=0.275, methanol).

Anal. Calcd. for C$_{18}$H$_{20}$N$_2$Cl$_2$O$_8$: C, 46.67; H, 4.35; N, 6.05; Cl, 15.31. Found: C, 46.76; H, 4.35; N, 6.08; Cl, 15.23.

EXAMPLE 62

(1R,2S,3R,5R)-5-(5,6-Dichloro-2-methyl-1H-benzimidazol-1-yl)-3-(hydroxymethyl)-1,2-cyclopentanediol (1R,2S,3R,5R)-3-(Acetoxymethyl)-5-(4,5-dichloro-2-nitroanilino)-1,2-cyclopentanediyl diacetate (1.29 g, 2.78 mmol) in n-propanol (100 mL) was shaken with Raney nickel (Aldrich, slurry in water, 200 mg wet) under hydrogen (40 psi) on a Parr shaker for 4 hours. Catalyst was filtered off with Celite and the volatiles were evaporated in vacuo. The residual oil was refluxed in 96% formic acid (45 mL) for 5 hours. Concentrated hydrochloric acid (5 mL) was added and reflux continued for an additional 4 hours. Volatiles were evaporated in vacuo and the residue was dissolved in 1N sodium hydroxide (10 mL). The solution was stirred at ambient temperature for 18 hours, neutralized with acetic acid, and concentrated in vacuo. The residue was chromatographed on silica gel. Elution with 15% methanol-chloroform gave (1R,2S,3R,5R)-5-(5,6-dichloro-2-methyl-1H-benzimidazol-1-yl)-3-(hydroxymethyl)-1,2-cyclopentanediol as white powder (236 mg, 26%), m.p. 198°–200° C.; $^1$H-NMR(DMSO-d$_6$) δ: 8.30 and 7.72 (both s, 1 each, 2 aromatic CH), 5.0–4.8 (m, 3,2 OH and NCH), 4.56 (t, J=5.1 Hz, 1, CH$_2$OH), 4.2–4.1 (m, 2,2 OCH), 3.8–3.5 (m, 2, CH$_2$O), 2.58 (s, 3, CH$_3$), 2.4–2.2 (m, 1, CH), 2.2–1.9 (m, 2, CH$_2$); mass spectrum(CI): 331(M+1); $[\alpha]^{20}_{589}$−13.5°, $[\alpha]^{20}_{578}$−13.9°, $[\alpha]^{20}_{546}$−15.9°, $[\alpha]^{20}_{436}$−30.3° (c=0.251, methanol).

Anal. Calcd. for C$_{14}$H$_{16}$N$_2$Cl$_2$O$_3$: C, 50.78; H, 4.87; N, 8.46; Cl, 21.41. Found: 50.68; H, 4.88; N, 8.39; Cl, 21.31.

EXAMPLE 63

(1R,4S)-4-Amino-2-cyclopentene-1-methanol

A mixture of (−)-(1S,4R)-4-amino-2ocyclopentene-1-carboxylic acid (Chiros Ltd., Cambridge, England; 40.00 g, 0.315 mole) in dry tetrahydrofuran (300 mL) was stirred in an ice bath while 1M lithium aluminum hydride in tetrahydrofuran (Aldrich, 485 mL) was added over 1.5 hours. The temperature during this addition was not allowed to exceed 0° C. The mixture was brought to ambient temperature and then to reflux over one hour and maintained at reflux for 2.5 hours. The mixture was allowed to cool to ambient temperature and sodium fluoride (89.6 g) was added and stirring continued for an additional 0.5 hour. The mixture was cooled (ice bath) and water (23 mL) added slowly. Stirring was continued for an additional 0.5 hour. The precipitate was filtered and extracted with 40% methanol-tetrahydrofuran (2×300 mL). The filtrate-wash was concentrated in vacuo to a colorless oil which darkened rapidly in air and light and was used immediately (Example 64). Such a sample was dried at ambient temperature/0.2 mm Hg to a pale yellow oil; $^1$H-NMR(DMSO-d$_6$) identical to that of the enantiomer described in Example 22, δ: 5.67 (m, 2, CH=CH), 3.8–3.7 (m, 1, CHN), 3.32 (d, J=6.0 Hz, overlapped by broad D$_2$O-exchangeable peak centered at 3.18, CH$_2$O, OH, NH$_2$ and H$_2$O in solvent), 2.58–2.56 (m, 1, H-1), 2.28–2.18 (m, 1, ½CH$_2$), 1.08–0.9 (m, 1, ½CH$_2$); mass spectrum( CI): 114(M+1); $[\alpha]^{20}_{589}$+55.0°, $[\alpha]^{20}_{578}$+58.3°, $[\alpha]^{20}_{546}$+67.4°, $[\alpha]^{20}_{436}$+119° (c=0.242, methanol).

Anal. Calcd. for C$_6$H$_{11}$NO.0.31 H$_2$O: C, 60.69; H, 9.86; N, 11.80. Found: 61.12; H, 9.79; N, 11.38.

EXAMPLE 64

(1R,4S)-[4-(4,5-Dichloro-2-nitroanilino)-2-cyclopenten-1-yl]methanol

The filtrate-wash from Example 63 was concentrated and t-butanol (400 mL) was added to the residual oil. This solution was used for the condensation with 1,2,4-trichloro-5-nitrobenzene (Aldrich, 71.3 g, 0.315 mole as 97%) by the method of Example 33. The reaction mixture, after evaporation of volatiles in vacuo, was chromatographed on a silica gel column eluted with 1:1 hexanes-ethyl acetate and ethyl acetate. Rechromatography of the crude product on silica gel was carried out with elution of by 4–6% methanol-chloroform. Combined product-containing fractions yielded 58 grams of reddish solid on evaporation of solvents. This solid was resolidified from ethyl acetate-hexanes to give (1R,4S)-[4-(4,5-dichloro-2-nitroanilino)-2-cyclopenten-1-yl]methanol as yellow powder (34.5 g, 36% from (−)-(1S,4R)-4-amino-2-cyclopentene-1-carboxylic acid); m.p. 95°–97° C.; $^1$H-NMR(DMSO-d$_6$) and mass spectrum(CI) identical with those of the enantiomer described in Example 53; $[\alpha]^{20}_{589}$−195°, $[\alpha]^{20}_{578}$−217°, $[\alpha]^{20}_{546}$−326° (c=0.350, methanol).

Anal. Calcd. for C$_{12}$H$_{12}$N$_2$Cl$_2$O$_3$: C, 47.55; H, 3.99; N, 9.24; Cl, 23.39. Found: C, 47.56; H, 4.01; N, 9.25; Cl, 23.30.

Continued elution of the column (above) gave additional yellow powder (18.0 g, 19%) which $^1$-NMR showed to be additional title compound contaminated by ca. 15% of (1R,4S)-[4-(2,5-dichloro-4-nitroanilino)-2-cyclopenten-1-yl]methanol.

EXAMPLE 65

(1R,2S,3S,5S)-3-(Acetoxymethyl)-5-(4,5-dichloro-2-nitroanilino)-1,2-cyclopentanediyl diacetate and (1S,2R,3S,5S)-3-(acetoxymethyl)-5-(4,5-dichloro-2-nitroanilino)-1,2-cyclopentanediyl diacetate (1R,4S)-[4-(4,5-Dichloro-2-nitroanilino)-2-cyclopenten-1-yl]methanol (17.00 g, 56.1 mmol) was hydroxylated and the mixture of triols was acetylated as in Example 38. The crude red oil isolated after acetylation was chromatographed on silica gel and a mixture of title compounds eluted with 2% methanol-chloroform. Fractional crystallization from ethyl acetate-hexanes gave (1R,2S,3S,5S)-3-(acetoxymethyl)-5-(4,5-dichloro-2-nitroanilino)-1,2-cyclopentanediyl diacetate as yellow needles in two crops (12.78 g, 49%), m.p. 127°–128° C.; $^1$H-NMR(DMSO-d$_6$) and mass spectrum (CI) identical to those of the racemic sample described in Example 1 and the enantiomer described in Example 55; $[\alpha]^{20}_{589}+106$ Ⓡ, $[\alpha]^{20}_{578}+119°$, $[\alpha]^{20}_{546}+184°$ (c=0.275, methanol).

Anal. Calcd. for $C_{18}H_{20}N_2Cl_2O_8$: C, 46.67; H, 4.35; N, 6.05; Cl, 15.31. Found: 46.74; H, 4.40; N, 6.09; Cl, 15.22.

Continued fractional crystallization of the mother liquor contents from ethyl acetate-hexanes gave (1S,2R,3S,5S)-3-(acetoxymethyl)-5-(4,5-dichloro-2-nitroanilino)-1,2-cyclopentanediyl diacetate as orange crystals (2.45 g, 10%), m.p. 122°–124° C.; $^1$H-NMR(DMSO-d$_6$) identical with that of the chiral sample described in Example 61.

Evaporation of combined mother liquors gave an additional 9.50 g (40%) of an approximately 1:1 (by $^1$H-NMR) mixture of the title compounds.

EXAMPLE 66

(1R,2S,3S,5S)-3-(Acetoxymethyl)-5-(5,6-dichloro-1H-benzimidazol-1-yl)-1,2-cyclopentanediyl diacetate (1R,2S,3S,5S)-3-(Acetoxymethyl)-5-(4,5-dichloro-2-nitroanilino)-1,2-cyclopentanediyl diacetate was converted to title compound as in Example 2. The crude product after formic acid treatment was chromatographed on silica gel with elution by 10% ethyl acetate-hexanes. Evaporation of product-containing fractions left (1R,2S,3S,5S)-3-(acetoxymethyl)-5-(5,6-dichloro-1H-benzimidazol-1-yl)-1,2-cyclopentanediyl diacetate as a white solid foam from ethyl acetate (1.85 g, 95%); $^1$H-NMR(DMSO-d$_6$) and mass spectrum(CI) identical to those of racemate described in Example 2 and enantiomer described in Example 56; $[\alpha]^{20}_{589}-25.5°$, $[\alpha]^{20}_{578}-27.0°$, $[\alpha]^{20}_{546}-31.2°$ (c=0.333, methanol).

Anal. Calcd. for $C_{19}H_{20}N_2Cl_2O_6 \cdot 0.1$ EtOAc: C, 51.54; H, 4.64; N, 6.20; Cl, 15.68. Found: C, 51.29; H, 4.69; N, 6.19; Cl, 15.91.

EXAMPLE 67

(1S,2R,3S,5S)-5-(5,6-Dichloro-1H-benzimidazol-1-yl)-3-(hydroxymethyl)-1,2-cyclopentanediol and (1R,2S,3S,5S)-5-(5,6-Dichloro-1H-benzimidazol-1-yl)-3-(hydroxymethyl)-1,2-cyclopentanediol An ca. 1:1 mixture of (1R,2S,3S,5S)-3-(acetoxymethyl)-5-(4,5-dichloro-2-nitroanilino)-1,2-cyclopentanediyl diacetate and (1S,2R,3S,5S)-3-(acetoxymethyl)-5-(4,5-dichloro-2-nitroanilino)-1,2-cyclopentanediyl diacetate (4.30 g, 9.28 mmol) was deacetylated with sodium carbonate (97 mg) in 1:1:1 water-ethanol-methanol (100 mL) at ambient temperature for 24 hours. The pH was adjusted to 7 with acetic acid and the volatiles removed in vacuo. The residual solid was extracted with methanol. The methanol filtrate was evaporated to dryness in vacuo. The residual solid was dissolved in ethanol (55 mL)-water (20 mL), adjusted to pH 5–6 with sulfuric acid, and refluxed with iron powder (325 mesh, 99.9%, Aldrich, 5.18 g, 93 mequiv) and iron(II) sulfate heptahydrate (Aldrich, 98+%, 1.30 g, 4.58 mequiv) for 4 hours. Solids were filtered off and the ethanol filtrate-wash concentrated to an oil. Triethylorthoformate (55 mL) and methanesulfonic acid (0.05 mL) were added to the oil and the resulting solution stirred at ambient temperature for 18 hours. Concentration in vacuo left an oil which was redissolved in 1N hydrochloric acid (50 mL)-dioxane(5 mL). After 2.5 hours, the pH was adjusted to 7 with 1N sodium hydroxide and the volatiles evaporated in vacuo. The residual solids were chromatographed on silica gel. Elution with 10–12% methanol-chloroform gave fractions containing (1S,2R,3S,5S)-5-(5,6-dichloro-1H-benzimidazol-1-yl)-3-(hydroxymethyl)-1,2-cyclopentanediol, which was isolated as white crystals (540 mg, 18%) after crystallization from ethyl acetate-hexanes, m.p. 201°–202 C.; $^1$H-NMR(DMSO-d$_6$) δ: 8.42, 8.07, and 7.92 (all s, 1 each, 3 benzimidazole CH), 5.1–4.8 (m overlapping d at 5.02, J=5.7 Hz, and d at 4.93, J=3.9 Hz, total 3, NCH and 2 OH), 4.54 (t, J=4.8 Hz, 1, OH), 4.2–4.0 (m, 2,2 OCH), 3.75–3.45 (m, 2, OCH$_2$), 2.4–1.9 (m, 3, CH$_2$ and CH); mass spectrum(CI): 317 (M+1); $[\alpha]^{20}_{589}-61.4°$, $[\alpha]^{20}_{578}-63.1°$, $[\alpha]^{20}_{546}-72.9°$ (c=0.350, methanol).

Anal. Calcd. for $C_{13}H_{14}N_2Cl_2O_3$: C, 49.23; H, 4.45; N, 8.83; Cl, 22.36. Found: C, 49.20; H, 4.45; N, 8.78; Cl, 22.37.

Continued elution of the column with 15–20% methanol-chloroform gave fractions containing a mixture of the title compounds followed by fractions containing only (1R,2S,3S,5S)-5-(5,6-dichloro-1H-benzimidazol-1-yl)-3-(hydroxymethyl)-1,2-cyclopentanediol, which was isolated as white crystals (605 mg, 21%) on crystallization from 10% methanol-ethyl acetate, m.p. 221°–222° C.; $^1$H-NMR(DMSO-d$_6$) and mass spectrum(CI) identical with those of the enantiomer described in Example 57; $[\alpha]^{20}_{589}+14.5°$, $[\alpha]^{20}_{578}+15.2°$, $[\alpha]^{20}_{546}+16.9°$ (c=0.290, methanol).

Anal. Calcd. for $C_{13}H_{14}N_2Cl_2O_3$: C, 49.23; H, 4.45; N, 8.83; Cl, 22.36. Found: C, 49.29; H, 4.46; N, 8.87; Cl, 22.26.

EXAMPLE 68

(1R,2S,3S,5S)-3-(Acetoxymethyl)-5-(2-bromo-5,6-dichloro-1H-benzimidazol-1-yl)-1,2,cyclopentanediyl diacetate (1R,2S,3S,5S)-3-(Acetoxymethyl)-5-(5,6-dichloro-1H-benzimidazol-1-yl)-1,2-cyclopentanediyl diacetate (1.40 g, 2.94 mmol) was brominated as in Example 3. Volatiles were removed in vacuo and the residue chromatographed on silica gel. Crude product eluted with 20–30% hexane-ethyl acetate as a colorless oil. A chloroform solution of the oil was washed with water in order to remove contaminating succinimide. The chloroform solution was dried (sodium sulfate) and evaporated to dryness in vacuo to give title compound as white solid foam from ethanol (760 mg, 50%); $^1$H-NMR (DMSO-d$_6$) and mass spectrum(CI) identical to racemate described in Example 3; $[\alpha]^{20}_{589}+43.8°$, $[\alpha]^{20}_{578}+45.2°$, $[\alpha]^{20}_{546}52.2°$ (c=0.345, methanol).

Anal. Calcd. for $C_{19}H_{19}N_2BrCl_6O_6$·0.05 EtOH: C, 43.74; H, 3.71; N, 5.34; total halogen as Cl, 20.28. Found: C, 43.74; H, 3.69; N, 5.35; total halogen as Cl, 20.41.

EXAMPLE 69

(1R,2S,3S,5S)-5-(2-Bromo-5,6-dichloro-1H-benzimidazol-1-yl)-3-(hydroxymethyl)-1,2-cyclopentanediol (1R,2S,3S,5S)-3-(Acetoxymethyl)-5-(5,6-dichloro-1H-benzimidazol-1-yl)-1,2-cyclopentanediyl diacetate (660 mg, 1.26 mmol) was deacetylated as in Example 4 to give title compound as white powder after solidification from 1:1 ethanol-methanol (415 mg, 83%), m.p. 213°–216° C.; $^1$H-NMR(DMSO-d$_6$) and mass spectrum(CI) identical with those of racemate described in Example 4; $[\alpha]^{20}_{589}+35.9°$, $[\alpha]^{20}_{578}+36.8°$, $[\alpha]^{20}_{546}+42.1°$ (c=0.340, methanol).

Anal. Calcd. for $C_{13}H_{13}N_2BrCl_2O_3$: C, 39.43; H, 3.31; N, 7.07; total halogen as Cl, 26.86. Found: C, 39.48; H, 3.29; N, 7.00; total halogen as Cl, 26.90.

EXAMPLE 70

(±)-4,5-Dichloro-N-(2-cyclopenten-1-yl)-2-nitroaniline

3-Aminocyclopentene hydrochloride (R. Vince and S. Daluge, J. Med. Chem. 1974, 17,578) (5.10 g, 42.8 mmol), 1,2,4-trichloro-5-nitrobenzene (Aldrich, 10.0 g, 42.8 mmol), and potassium carbonate (98%, Aldrich, 15.00 g, 107 mmol) were refluxed in t-butyl alcohol (100 mL) under nitrogen for 24 hours. Volatiles were evaporated in vacuo and the residue chromatographed on silica gel. Title compound was eluted with 20–30% chloroform-hexanes as an orange powder (5.14 g, 44%), m.p. 85°–86° C.; $^1$H-NMR(DMSO-d$_6$) δ: 8.27 (s, 1, aromatic CH), 7.88 (d, J=7.3 Hz, 1, NH), 7.48 (s, 1, aromatic CH), 6.2–6.0 (m, 1, =CH), 6.0–5.8 (m, 1, =CH), 5.0– 4.7 ( m, 1, NCH), 2.6–2.2 (m overlapping solvent, 3 CH), 1.8–1.5 (m, 1, ½CH$_2$); mass spectrum(CI): 273 (M+1).

Anal. Calcd. for $C_{11}H_{10}N_2Cl_2O_2$: C, 48.37; H, 3.69; N, 10.26; Cl, 25.96. Found: 48.39; H, 3.72; N, 10.28; Cl, 25.87.

EXAMPLE 71

(±)-(1R*,2S*,3R*)-3-(4,5-Dichloro-2-nitroanilino)-1,2-cyclopentanediol and
(±)-(1S,2R*,3R*)-3-(4,5-dichloro-2-nitroanilino)-1,2-cyclopentanediol (±)-4,5-Dichloro-N-(2-cyclopenten-1-yl)-2-nitroaniline (6.30 g, 23.1 mmol) was hydroxylated as in Example 38. Volatiles were evaporated in vacuo and the residue was chromatographed on silica gel. A mixture of title compounds was eluted with 10% methanol-chloroform as a orange solid (7.00 g). Crystallization from ethanol-water gave (±)-(1S*,2R*,3R*)-3-(4,5-dichloro-2-nitroanilino)-1,2-cyclopentanediol as orange powder (4.03 g, 57%), m.p. 134°–136° C.; $^1$H-NMR(DMSO-d$_6$) δ: 8.72 (d, J=7.6 Hz, 1, NH), 8.25 and 7.36 (both s, 1 each, 2 aromatic CH), 5.25 (d, J=4.5 Hz, 1, OH), 4.80 (d, J=5.1 Hz, 1, OH), 4.14–3.86 (m, 3,2 OCH and 1 NCH), 2.2–2.1 (m, 1, CH), 1.8–1.4 (m, 3, CH and CH$_2$); mass spectrum(CI): 307(M+1).

Anal. Calcd. for $C_{11}H_{12}N_2Cl_2O_4$: C, 43.02; H, 3.94; N, 9.12; Cl, 23.09. Found: C, 43.09; H, 3.99; N, 9.03; Cl, 23.03.

Concentration of the mother liquor gave additional orange solid (2.86 g) which 1H-NMR showed to be an approximately 1:1 mixture of (±)-(±)-(1R*,2S*,3R*)-3-(4,5-dichloro-2-nitroanilino)-1,2-cyclopentanediol (NMR spectrum described in Example 16) and (±)-(1S*,2R*,3R*)-3-(4,5-dichloro-2-nitroanilino)-1,2-cyclopentanediol.

EXAMPLE 72

(±)-(1S*,2R*,3R*)-3-(5,6-Dichloro-1H-benzimidazol-1-yl)-1,2-cyclopentanediol (±)-(1S*,2R*,3R*)-3-(4,5-Dichloro-2-nitroanilino)-1,2-cyclopentanediol (3.77 g, 12.3 mmol) in isopropanol (250 mL) was shaken in a Parr shaker with Raney nickel (Aldrich, prewashed with water until neutral, ca. 1 tsp) under hydrogen (50 psi) for 2 hours, at which point uptake of hydrogen had ceased. TLC (silica gel, methanol:chloroform/1:10) shows one spot at lower $R_f$ than starting material. The catalyst was filtered off (Celite) and volatiles evaporated to leave a glass which was refluxed in formic acid (65 mL) for 40 minutes. The formic acid was evaporated and the residual oil dissolved in ethanol (50 mL) and adjusted to pH 13 with 5N sodium hydroxide. After stirring at ambient temperature for 18 hours, the pH was adjusted to 7 with hydrochloric acid and the volatiles removed by evaporation in vacuo. The residue was triturated with methanol. The methanol solution was evaporated to dryness to give white solid which contained product and some salts (7.41 g). A portion of this solid (1.05 g) was chromatographed on silica gel and product was eluted with 6–8% methanol-chloroform as white powder, after solidification from ethanol (350 mg), m.p. 180°–182° C.; $^1$H-NMR(DMSO-d$_6$) δ: 8.46, 8.08, and 7.93 (all s, 1 each, 3 aromatic CH), 4.96 (d, J=4.7 Hz, 1, OH), 4.92–4.85 (m, 1, NCH), 4.81 (d, J=5.9 Hz, 1, OH), 4.19–4.11 (m, 1, OCH), 4.08–3.93 (m, 1, OCH), 2.38–2.04 (m, 2, CH$_2$), 2.03–1.72 (m, 2, CH$_2$); mass spectrum(CI): 287 (M+1).

Anal. Anal. Calcd. for $C_{12}H_{12}N_2Cl_2O_2$: C, 50.19; H, 4.21; N, 9.76; Cl, 24.69. Found: C, 50.18; H, 4.24; N, 9.74; Cl, 24.60.

EXAMPLE 73

(±)-(1S*,2R*,3R*)-3-(2-Bromo-5,6-dichloro-1H-benzimidazol-1-yl)-1,2-cyclopentanediyl diacetate (±)-(1S*,2R*,3R*)-3-(5,6-Dichloro-1H-benzimidazol-1-yl)-1,2-cyclopentanediol (3.00 g, 10.5 mmol) was acetylated and brominated as in Example 39 and the title compound eluted from a silica gel column with 1% methanol-chloroform to give product as tan solid foam (2.86 g, 66%). Further purification of such a sample by chromatography on silica gel with elution by 10% hexanes-chloroform followed by resolidification from methanol gave (±)-(1S*,2R*,3R*)-3-(2-bromo-5,6-dichloro-1H-cyclopentanediyl diacetate as yellow powder, m.p. 203°–205° C.; $^1$H-NMR (DMSO-d$_6$) δ: 8.03 and 7.93 (both s, 1 each 2 aromatic CH), 5.42–5.33 (m, 3,2 OCH and NCH), 2.69–2.62 (m, 1, ½CH$_2$), 2.28–2.09 (m, 6, CH$_2$, CH, and CH$_3$), 1.54–1.51 (m, 3, CH$_3$); mass spectrum (CI): 455 (7.1), 453 (47), 451 (100), 449 (455, M+1).

Anal. Calcd. for $C_{16}H_{15}N_2Cl_2BrO_4$: C, 42.69; H, 3.36; N, 6.22; total halogen as Cl, 23.63. Found: C, 42.77; H, 3.39; N, 6.17; total halogen as Cl, 23.62.

I claim:

1. A method of treating a host having an HBV infection which comprises administering to said host a therapeutically effective amount of a compound of formula (I) or (I-1)

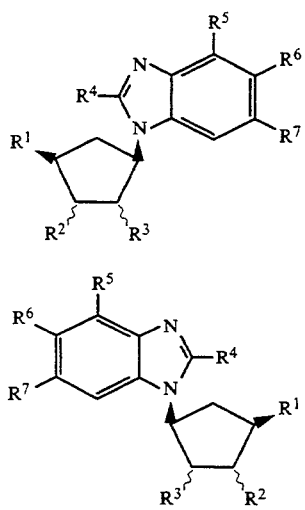

wherein $R^1$ is H, $CH_3$ or $CH_2OH$;
$R^2$ is H or OH;
$R^3$ is H or OH;
or $R^2$ and $R^3$ together form a bond;
$R^4$ is H, Cl, Br, I, $C_{1-4}$ alkyl, $C_{3-7}$cycloalkyl, $C_{3-7}$cycloalkyl$C_{1-4}$alkyl, $C_{1-4}$ perfluoroalkyl, $NH_2$, $C_{1-4}$ alkylamino, $C_{1-4}$ dialkylamino, $C_{3-7}$cycloalkylamino, di$C_{3-7}$cycloalkylamino, N-$C_{1-4}$alkyl-N-$C_{3-7}$cycloalkylamino, N-$C_{1-4}$alkyl-N-$C_{3-7}$cycloalkyl$C_{1-4}$alkylamino, di$C_{3-7}$cycloalkyl$C_{1-4}$alkylamino, $C_{3-7}$cycloalkyl$C_{1-4}$alkylamino, N-$C_{3-7}$cycloalkyl-N-$C_{3-7}$cycloalkyl$C_{1-4}$alkylamino, SH, $C_{1-4}$ alkylthio, $C_{6-10}$aryl$C_{1-4}$alkylthio, OH, $C_{1-4}$ alkoxy, $C_{6-10}$aryl$C_{1-4}$alkoxy or $C_{6-10}$aryl$C_{1-4}$alkyl; and $R^5$, $R^6$ and $R^7$ are independently selected from H, F, Cl, Br, I, $CF_3$ and $CH_3$, provided that at least one of $R^1$, $R^2$ and $R^3$ is or contains OH;
or a pharmaceutically acceptable derivative thereof.

2. A method according to claim 1 wherein said host is a human being.

3. A method according to claim 2 wherein said compound is a compound of formula (I-1).

4. A method according to claim 1 wherein said compound is (1R,2S,3S,5S)-5-(2-bromo-5,6-dichloro-1H-benzimidazol-1-yl)-3-(hydroxymethyl)-1,2-cyclopentanediol or a pharmaceutically acceptable derivative thereof.

5. A method according to claim 1 wherein said compound is (1S,2R,3R,5R)-5-(2-bromo-5,6-dichloro-1H-benzimidazol-1-yl)-3-(hydroxymethyl)-1,2-cyclopentanediol or a pharmaceutically acceptable derivative thereof.

6. A method according to claim 1 wherein said compound is ±-(1R*,2S*,3S*,5S*)-5-(2-bromo-5,6-dichloro-1H-benzimidazol-1-yl)-3-(hydroxymethyl)-1,2-cyclopentanediol or a pharmaceutically acceptable derivative thereof.

7. A method according to claim 1 wherein said compound is ±-(1R*,2R*,4S*)-2-(2-bromo-5,6-dichloro-1H-benzimidazol-1-yl)-4-(hydroxymethyl)cyclopentanol or a pharmaceutically acceptable derivative thereof.

8. A method according to claim 1 wherein said compound is ±-(1R*,2S*,3S*,5S*)-5-(5,6-dichloro-2-methyl-1H-benzimidazol-1-yl)-3-(hydroxymethyl)-1,2-cyclopentanediol or a pharmaceutically acceptable derivative thereof.

9. A method of treating a host having an HBV infection which comprises administering to said host a therapeutically effective amount of a compound of formula (IA) or (IA-1)

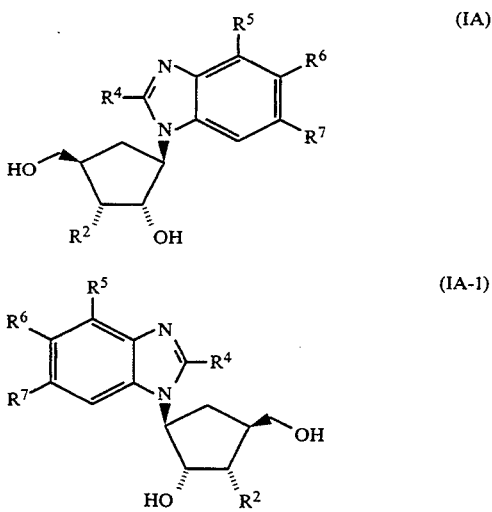

wherein $R^2$ is H or OH;
$R^4$ is H, Cl, Br, I, $C_{1-4}$ alkyl, $C_{3-7}$cycloalkyl, $C_{3-7}$cycloalkyl$C_{1-4}$alkyl, $C_{1-4}$ perfluoroalkyl, $NH_2$, $C_{1-4}$ alkylamino, $C_{1-4}$ dialkylamino, $C_{3-7}$cycloalkylamino, di$C_{3-7}$cycloalkylamino, N-$C_{1-4}$alkyl-N-$C_{3-7}$cycloalkylamino, N-$C_{1-4}$alkyl-N-$C_{3-7}$cycloalkyl$C_{1-4}$alkylamino, di$C_{3-7}$cycloalkyl$C_{1-4}$alkylamino, $C_{3-7}$cycloalkyl$C_{1-4}$alkylamino, N-$C_{3-7}$cycloalkyl-N-$C_{3-7}$cycloalkyl$C_{1-4}$alkylamino, SH, $C_{1-4}$ alkylthio, $C_{6-10}$aryl$C_{1-4}$alkylthio, OH, $C_{1-4}$ alkoxy, $C_{6-10}$aryl$C_{1-4}$alkoxy or $C_{6-10}$aryl$C_{1-4}$alkyl; and
$R^5$, $R^6$ and $R^7$ are independently selected from H, F, Cl, Br, I, $CF_3$ and $CH_3$;
or a pharmaceutically acceptable derivative thereof.

10. A method according to claim 9 wherein said host is a human being.

11. A method according to claim 10 wherein said compound is a compound of formula (IA-1).

12. A method according to claim 9 wherein said compound is (1R,2S,3S,5S)-5-(2-bromo-5,6-dichloro-1H-benzimidazol-1-yl)-3-(hydroxymethyl)-1,2-cyclopentanediol, or a pharmaceutically acceptable derivative thereof.

13. A method according to claim 9 wherein said compound is (1S,2R,3R,5R)-5-(2-bromo-5,6-dichloro-1H-benzimidazol-1-yl)-3-(hydroxymethyl)-1,2-cyclopentanediol.

14. A method according to claim 1 wherein said compound or a pharmaceutically acceptable derivative thereof is administered orally to said host.

15. A method according to claim 1 wherein said compound or a pharmaceutically acceptable derivative thereof is administered parenterally to said host.

16. A method according to claim 9 wherein said compound or a pharmaceutically acceptable derivative thereof is administered orally to said host.

17. A method according to claim 9 wherein said compound or a pharmaceutically acceptable derivative thereof is administered parenterally to said host.

18. A method according to claim 1 whereto stud compound or a pharmaceutically acceptable derivative thereof is administered in unit dose form to said host.

19. A method according to claim I wherein said compound is administered in an effective HBV infection treatment amount.

20. A method according to claim 9 wherein said compound is administered in an effective HBV infection treatment amount.

* * * * *